United States Patent
White et al.

(10) Patent No.: US 10,101,250 B2
(45) Date of Patent: Oct. 16, 2018

(54) MANIPULATION OF CELL NUCLEI IN A MICRO-FLUIDIC DEVICE

(71) Applicant: Berkeley Lights, Inc., Emeryville, CA (US)

(72) Inventors: Mark P. White, San Francisco, CA (US); Randall D. Lowe, Jr., Emeryville, CA (US)

(73) Assignee: Berkeley Lights, Inc., Emeryville, CA (US)

(*) Notice: Subject to any disclaimer, the term of this patent is extended or adjusted under 35 U.S.C. 154(b) by 11 days.

(21) Appl. No.: 15/136,763

(22) Filed: Apr. 22, 2016

(65) Prior Publication Data

US 2016/0370266 A1    Dec. 22, 2016

Related U.S. Application Data

(60) Provisional application No. 62/151,334, filed on Apr. 22, 2015.

(51) Int. Cl.
  *G01N 1/34* (2006.01)
  *B01L 3/00* (2006.01)
  (Continued)

(52) U.S. Cl.
  CPC .......... *G01N 1/34* (2013.01); *B01L 3/502761* (2013.01); *B03C 5/005* (2013.01); *B03C 5/026* (2013.01); *C12Q 1/6806* (2013.01); *G01N 27/44704* (2013.01); *G01N 27/44791* (2013.01); *B01L 2200/0668* (2013.01); *B01L 2300/0816* (2013.01); *B01L 2300/0819* (2013.01); *B01L 2300/0877* (2013.01);
  (Continued)

(58) Field of Classification Search
  None
  See application file for complete search history.

(56) References Cited

U.S. PATENT DOCUMENTS

| 6,294,063 B1 | 9/2001 | Becker et al. |
| 6,383,813 B1 * | 5/2002 | Baxter .................. C12M 35/00 435/285.1 |

(Continued)

FOREIGN PATENT DOCUMENTS

| EP | 1065378 A2 | 1/2001 |
| EP | 2316565 A1 | 5/2011 |

(Continued)

OTHER PUBLICATIONS

Hsuan et al "Automatic microfluidic platform for cell separation and nucleus collection" Biomed Microdevices, 2007, 9: 533-543.*

(Continued)

*Primary Examiner* — Betty J Forman
(74) *Attorney, Agent, or Firm* — Kenneth E. Horton; Kirton McConkie

(57) ABSTRACT

Aspects of the present disclosure are directed to the manipulation of a cell nucleus in a micro-fluidic device as well as compositions, systems, and kits for performing such methods. In some aspects, the disclosure provides methods for placing one or more selected cell nuclei into an isolation region of a sequestration pen in a micro-fluidic device. The isolated nucleus/nuclei may then be retrieved from the isolation region of the sequestration pen and used in any desired downstream assay or process.

26 Claims, 17 Drawing Sheets

(51) Int. Cl.
  *B03C 5/00* (2006.01)
  *B03C 5/02* (2006.01)
  *C12Q 1/6806* (2018.01)
  *G01N 27/447* (2006.01)

(52) U.S. Cl.
  CPC .................. *B01L 2400/0424* (2013.01); *B01L 2400/0454* (2013.01); *B01L 2400/0457* (2013.01); *B01L 2400/086* (2013.01); *B03C 2201/26* (2013.01)

(56) References Cited

U.S. PATENT DOCUMENTS

| | | |
|---|---|---|
| 6,942,776 B2 | 9/2005 | Medoro |
| 7,090,759 B1 | 8/2006 | Seul |
| 2002/0088712 A1 | 7/2002 | Miles |
| 2003/0008364 A1 | 1/2003 | Wang et al. |
| 2003/0224528 A1 | 12/2003 | Chiou et al. |
| 2004/0072278 A1 | 4/2004 | Chou et al. |
| 2004/0191789 A1 | 9/2004 | Manaresi et al. |
| 2005/0112548 A1 | 5/2005 | Segawa et al. |
| 2005/0175981 A1 | 8/2005 | Voldman et al. |
| 2006/0057581 A1* | 3/2006 | Karlsen ............ B01L 3/502761 435/6.12 |
| 2006/0091015 A1 | 5/2006 | Lau |
| 2006/0263612 A1* | 11/2006 | Chen ....................... B32B 27/00 428/447 |
| 2007/0095669 A1 | 5/2007 | Lau et al. |
| 2007/0242105 A1 | 10/2007 | Srinivasan |
| 2008/0302732 A1 | 12/2008 | Soh et al. |
| 2009/0098541 A1* | 4/2009 | Southern ........... B01L 3/502753 435/6.11 |
| 2009/0170186 A1 | 7/2009 | Wu et al. |
| 2009/0305224 A1 | 12/2009 | He et al. |
| 2010/0000620 A1 | 1/2010 | Fouillet et al. |
| 2010/0003666 A1 | 1/2010 | Lee et al. |
| 2010/0021910 A1* | 1/2010 | Cao ................... B01L 3/502753 435/6.11 |
| 2010/0101960 A1 | 4/2010 | Ohta et al. |
| 2011/0117634 A1 | 5/2011 | Halamish et al. |
| 2011/0143964 A1 | 6/2011 | Zhou et al. |
| 2012/0024708 A1 | 2/2012 | Chiou et al. |
| 2012/0118740 A1 | 5/2012 | Garcia et al. |
| 2012/0208266 A1 | 8/2012 | Bookbinder et al. |
| 2012/0325665 A1 | 12/2012 | Chiou et al. |
| 2013/0118905 A1 | 5/2013 | Morimoto et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0252258 A1 | 9/2013 | Bocchi |
| 2013/0261021 A1 | 10/2013 | Bocchi et al. |
| 2013/0288065 A1 | 10/2013 | Chen et al. |
| 2014/0116881 A1 | 5/2014 | Chapman et al. |
| 2015/0018226 A1 | 1/2015 | Hansen et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2016/0171686 A1 | 6/2016 | Du et al. |
| 2016/0184821 A1 | 6/2016 | Hobbs et al. |
| 2016/0193604 A1 | 7/2016 | McFarland et al. |
| 2016/0252495 A1 | 9/2016 | Ricicova et al. |
| 2016/0312165 A1 | 10/2016 | Lowe, Jr. et al. |

FOREIGN PATENT DOCUMENTS

| | | |
|---|---|---|
| EP | 2685266 A1 | 3/2012 |
| WO | 2010147078 A1 | 12/2010 |
| WO | 2013130714 A1 | 9/2013 |

OTHER PUBLICATIONS

Chiou et al., Massively Parallel Manipulation of Single Cells and Microparticles Using Optical Images, Nature 436:370-73 (2005).
Lin et al., An Optically Induced Cell Lysis Device Using DEP, Applied Physics Letters 94:033901 (2009).
Chung et al., DNA-tethered Membranes Formed by Giant Vesicle Rupture, Journal of Structural Biology 168:190-99 (2009).
Valley et al., Optoelectronic Tweezers as a Tool for Parallel Single-Cell Manipulation and Stimulation, IEEE Transactions on Biomedical Circuits and Systems 3(6):424-30 (2009).
Lee et al., Development of Macroporous PEG Hydrogel Arrays within Microfluidic Channels , Biomacromolecules 13:11(12): 3316-3324 (2010).
Somaweera et al., Generation of a Chemical Gradient Across an Array of 256 Cell Cultures in a Single Chip, Analyst., Oct. 7, 2013, vol. 138, No. 19, pp. 5566-5571.
Lowe,"Controlled Vapor Deposition of Azide-terminated Siloxane Monolayers: a Platform for Tailoring Oxide Surfaces", Stanford University, Aug. 2011.

\* cited by examiner

MANIPULATION OF CELL NUCLEI IN A MICRO-FLUIDIC DEVICE

CROSS REFERENCE

This application is a non-provisional of, and thus claims the benefit of and/or priority to, U.S. provisional patent application Ser. No. 62/151,334, filed on Apr. 22, 2015, the entire contents of which are incorporated herein by reference. This application cross-references U.S. application Ser. No. 15/135,707, entitled "Microfluidic Cell Culture", filed on Apr. 22, 2016, which disclosure is herein incorporated by reference in its entirety.

BACKGROUND

The analysis of individual intact eukaryotic cells, or populations of isolated cells, can be hindered due to many factors, including the morphology of the cell (e.g., differentiated neurons), the source of the cell (e.g., complex tissue), or the fact that the cells have been treated with a preservative or are otherwise in a non-viable or compromised state (e.g., frozen, fixed, paraffin embedded, attached to a slide, etc.). Such difficulties have resulted in a loss of valuable information that could be gained were the cells more amenable to manipulation. Among other advantages, the present disclosure provides methods and systems for isolating individual nuclei derived from a cell sample (e.g., fixed or frozen samples), thereby enabling the analysis of cell phenotypes and genotypes from cell sources that were previously considered of limited value.

SUMMARY

In one aspect, the present invention relates to a method of isolating a cell nucleus. The method comprises flowing a medium comprising a cell nucleus into a flow region of a microfluidic device, wherein said flow region is in fluid connection with a first isolation region, and wherein said microfluidic device comprises a substrate configured to selectively generate forces that move micro-objects. The method further comprises moving said cell nucleus from said flow region to said first isolation region, wherein the flow of said medium in said flow region does not penetrate into said first isolation region.

In various embodiments, moving said cell nucleus from said flow region to said first isolation region comprises using said forces selectively generated by said substrate.

In various embodiments, moving said cell nucleus from said flow region to said first isolation region comprises tilting said microfluidic device such that gravity acts upon said cell nucleus and pulls it into or toward said first isolation region.

In various embodiments, said flow region comprises a flow channel in fluid connection with said first isolation region, and wherein flowing a medium comprising said cell nucleus comprises flowing said medium into said flow channel.

In various embodiments, said micro-fluidic device comprises a first sequestration pen, and wherein said first isolation region is located within said first sequestration pen.

In various embodiments, the method further comprises detecting a characteristic of said cell nucleus.

In various embodiments, detecting a characteristic of the cell nucleus is performed prior to said moving step of the method.

In various embodiments, said micro-fluidic device comprises a plurality of sequestration pens in fluid connection with said flow channel, each sequestration pen of said plurality having a corresponding isolation region.

In various embodiments, said flowing medium comprises a plurality of cell nuclei and said method further comprises moving said plurality of cell nuclei into said corresponding isolation region(s) of one or more sequestration pens of said plurality.

In various embodiments, the method further comprises selecting a first sub-set of cell nuclei from said plurality of cell nuclei that have a first predetermined characteristic, and moving said selected first sub-set of cell nuclei to the corresponding isolation region(s) of one or more first sequestration pens of said plurality of sequestration pens.

In various embodiments, the method further comprises selecting at least a second sub-set of cell nuclei from said plurality of cell nuclei that have a second predetermined characteristic, and moving said selected second sub-set of cell nuclei to the corresponding isolation region(s) of one or more second sequestration pens of said plurality of sequestration pens.

In various embodiments, only one cell nucleus is moved to an isolation region of a sequestration pen.

In various embodiments, said cell nuclei are contacted with a detectable binding agent.

In various embodiments, said binding agent is an antibody.

In various embodiments, said binding agent comprises a fluorescent label.

In various embodiments, moving said nuclei comprises generating dielectrophoresis (DEP) forces that attract or repel said cell nucleus.

In various embodiments, generating said DEP forces comprises activating DEP electrodes located at the surface of said substrate.

In various embodiments, said DEP electrodes are optically actuated.

In various embodiments, said DEP electrodes are virtual electrodes.

In various embodiments, said DEP electrodes are phototransistors.

In various embodiments, said DEP electrodes is controlled by a photo-actuated transistor.

In various embodiments, said DEP electrodes is controlled by an electrically-actuated transistor.

In various embodiments, said DEP electrodes is controlled independently of the other DEP electrodes.

In various embodiments, the method further comprises determining a genetic characteristic of one or more of said isolated cell nuclei.

In various embodiments, said determining step comprises extracting nucleic acids from said one or more of said isolated cell nuclei and performing one or more genetic analysis tests on said nucleic acids.

In various embodiments, said genetic characteristic is selected from the group consisting of: copy number of a genetic region, a mutation, a duplication, a single nucleotide polymorphism, an insertion, an inversion, a nucleic acid modification, a chromosomal feature, a difference compared to a reference nucleic acid sample, epigenetic variation, and combinations thereof.

In various embodiments, said one or more of said isolated cell nuclei are exported from said micro-fluidic device prior to performing said determining step.

In various embodiments, the cell nuclei are derived from a eukaryotic cell selected from the group consisting of: fungi, plants, protists, and animals.

In various embodiments, the cell nuclei are derived from a mammal or a human.

In various embodiments, the cell nuclei are derived from a tissue selected from the group consisting of: epithelial cell types (e.g., neuronal cell types, epidermal cells, cochlear hair cells, or the like), mesodermal cell types (e.g., muscle, fat, bone marrow, blood, or the like), endodermal cell types (e.g., intestinal cells or the like), blood cells (e.g., B cells, T cells, NK cells, macrophages), or tissues exhibiting a disease phenotype (e.g., cancer cells, inflamed cells, cells infected with a bacterial, fungal, protozoan, or viral pathogen).

In various embodiments, the method further comprises comprising harvesting said cell nuclei from one or more cells.

In various embodiments, said harvesting comprises one or more of: disrupting the cytoplasmic membrane and/or cell wall of said cell; contacting said cell nuclei with an enzyme (e.g., DNAse, collagenase, hyaluronidase); contacting said cell nuclei with a chelating agent (e.g., EDTA); and contacting said cell nuclei with one or more blocking agents (e.g., BSA, serum, polymers, detergents).

In various embodiments, the cell nuclei are derived from live cells.

In various embodiments, the cell nuclei are derived from non-viable cells.

In various embodiments, said non-viable cells are cells that have been frozen and thawed.

In various embodiments, said non-viable cells are cells that have been chemically fixed.

In various embodiments, the non-viable cells are derived from a formalin fixed paraffin embedded (FFPE) sample.

In various embodiments, the method further comprises de-waxing and rehydrating the sample.

In various embodiments, the cell nuclei are derived from a cancer cell.

In various embodiments, the cancer is selected from the group consisting of: breast cancer, large intestinal cancer, lung cancer, small lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, vaginal carcinoma, Hodgkin's disease, non-Hodgkin's lymphoma, esophageal cancer, small intestine cancer, endocrine cancer, thyroid cancer, parathyroid cancer, adrenal cancer, chronic or acute leukemia, soft tissue tumor, urethral cancer, penile cancer, prostate cancer, lymphocytic lymphoma, bladder carcinoma, kidney cancer, ureter cancer, renal carcinoma, renal pelvic carcinoma, CNS tumor, primary CNS lymphoma, bone marrow tumor, brain stem nerve gliomas, pituitary adenoma, testicular cancer, oral cancer, pharyngeal cancer, and uveal melanoma.

In various embodiments, the flow region, flow channel, isolation regions, and/or sequestration pens are pre-treated with a blocking solution to prevent or reduce nuclei adherence.

In various embodiments, the blocking solution comprises one or more of: serum, BSA, polymer, detergent, enzymes, or any combination thereof.

In various embodiments, the microfluidic device comprises a substrate surface and the blocking solution comprises a blocking agent that binds to substrate surface.

In various embodiments, the microfluidic device comprises a substrate surface that comprises a coating material.

In various embodiments, the coating material comprises molecules having a linking group and an alkyl moiety, wherein the linking group is covalently bonded to the substrate.

In various embodiments, the alkyl moiety is a fluoroalkyl group.

In various embodiments, the alkyl moiety is a perfluoroalkyl group.

In various embodiments, the linking group is a siloxy linking group.

In various embodiments, the alkyl moiety comprises a linear chain of carbons comprising at least 10 carbon atoms (e.g., at least 12, 14, 16, 18, 20, 22, or more carbon atoms).

In various embodiments, the molecules of the coating material form a densely-packed monolayer structure.

In various embodiments, the coating material comprises molecules having a linking group and a cationic moiety and/or an anionic moiety, wherein the linking group is covalently bonded to the substrate.

In various embodiments, the cationic moiety comprises a quaternary ammonium group.

In various embodiments, the anionic moiety comprises a phosphonic acid, carboxylic acid, or sulfonic acid.

In various embodiments, the coating material comprises molecules having a linking group and a zwitterionic moiety (e.g., capable of ionically bonding with a blocking agent).

In various embodiments, the zwitterionic moiety is selected from carboxybetaines, sulfobetaines, sulfamic acids, and amino acids.

In various embodiments, the coating material comprises a polymer comprising alkylene ether moieties, saccharide moieties, or amino acid moieties.

In various embodiments, the coating material comprises dextran.

In various embodiments, the coating material comprises poly-ethylene glycol.

In another aspect, the present invention relates to a method of identifying a cell nucleus associated with one or more characteristics wherein the cell nucleus is identified within a microfluidic device. The method further comprises repositioning said cell nucleus within the microfluidic device using dielectrophoretic force responsive to identifying that the cell nucleus is associated with a characteristic.

In various embodiments, the microfluidic device comprises a plurality of inner surfaces, wherein the plurality of inner surfaces have been treated with a blocking solution to prevent or reduce nuclei adherence.

In various embodiments, the blocking solution comprises a polymer comprising alkylene ether moieties.

In various embodiments, the polymer comprises polyethylene glycol.

In various embodiments, the blocking solution comprises a polymer comprising saccharide moieties.

In various embodiments, the blocking solution comprises dextran.

In various embodiments, the blocking solution comprises a polymer comprising amino acid moieties.

In various embodiments, the blocking solution comprises albumin.

In various embodiments, the microfluidic device comprises a substrate surface that has been coated with a coating material.

In various embodiments, the coating material comprises molecules having a linking group and an alkyl moiety, wherein the linking group is covalently bonded to the substrate surface.

In various embodiments, the alkyl moiety is a fluoroalkyl group.

In various embodiments, the alkyl moiety is a perfluoroalkyl group.

In various embodiments, the linking group is a siloxy linking group.

In various embodiments, the alkyl moiety comprises a linear chain of carbons comprising at least 10 carbon atoms (e.g., at least 12, 14, 16, 18, 20, 22, or more carbon atoms).

In various embodiments, the molecules of the coating material form a densely-packed monolayer structure.

In various embodiments, the coating material comprises molecules having a linking group and a cationic moiety and/or an anionic moiety, wherein the linking group is covalently bonded to the substrate surface.

In various embodiments, the cationic moiety comprises a quaternary ammonium group.

In various embodiments, the anionic moiety comprises a phosphonic acid, carboxylic acid, or sulfonic acid.

In various embodiments, the coating material comprises molecules having a linking group and a zwitterionic moiety (e.g., capable of ionically bonding with a blocking agent).

In various embodiments, the zwitterionic moiety is selected from carboxybetaines, sulfobetaines, sulfamic acids, and amino acids.

In various embodiments, the coating material comprises a polymer comprising alkylene ether moieties, saccharide moieties, or amino acid moieties.

In various embodiments, the coating material comprises dextran.

In various embodiments, the coating material comprises poly-ethylene glycol.

In various embodiments, the coating material comprises albumin.

In various embodiments, the one or more characteristics include the morphology of the cell nuclei.

In various embodiments, the one or more characteristics include the cell nucleus being labelled with a detectable binding agent.

In various embodiments, the one or more characteristics include the intensity of the binding agent.

In various embodiments, the one or more characteristics are identified using a machine learning algorithm.

In various embodiments, the microfluidic device comprises a flow region and a first sequestration pen, and wherein repositioning the cell nucleus in the microfluidic device comprises moving the cell nucleus from the flow region to the first sequestration pen using dielectrophoretic force.

In various embodiments, the microfluidic device comprises a first sequestration pen and a second sequestration pen, and repositioning the cell nucleus in the microfluidic device comprises moving the cell nucleus from the first sequestration pen to the second sequestration pen using dielectrophoretic force.

In various embodiments, repositioning the cell nuclei in the microfluidic device comprises moving the cell nuclei to a portion of the microfluidic device for export using dielectrophoretic force.

In various embodiments, repositioning the cell nuclei in the microfluidic device comprises moving the cell nuclei to a portion of the microfluidic device configured for electrowetting using dielectrophoretic force.

DETAILED DESCRIPTION OF EXEMPLARY EMBODIMENTS

Figure 1:
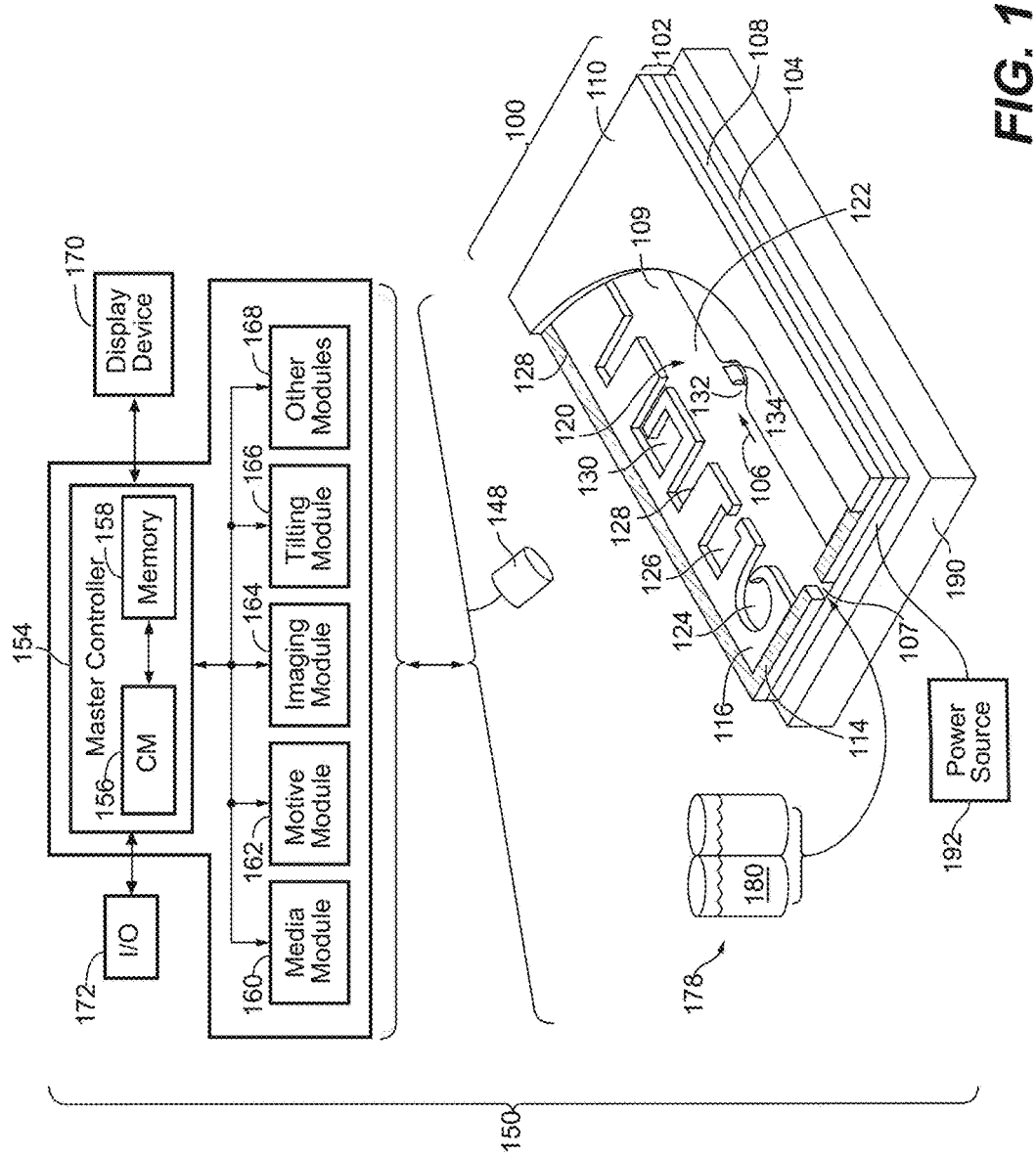
FIG. 1 illustrates an example of a system for use with a microfluidic device and associated control equipment according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 300 times the length, at least 400 times the length, at least 500 times the length, or longer. In some embodiments, the length of a flow channel is in the range of from about 20,000 microns to about 100,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells including but not limited to T cells, B cells, Natural Killer Cells, Macrophages, Dendritic Cells and the like, hybridomas, cultured cells, cells from a cell line, cancer cells including but not limited to circulating tumor cells, infected cells, transfected and/or transformed cells including but not limited to CHO cells, reporter cells, prokaryotic cell, and the like); biological organelles (e.g. nuclei); vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated microbeads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to fluidic media, "diffuse" and "diffusion" refer to thermodynamic movement of a component of fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1 illustrates an example of a system 150 which can be used to control a microfluidic device 100 (e.g. a microfluidic device of the present invention) in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having one or more openings in fluidic communication with flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120 and the enclosure 102. Depending on the embodiment, the height of the enclosure 102 (i.e. the distance from the cover 110 to the support structure 104) can range from 40 microns to 2 mm. In most embodiments, the height of the enclosure 102 will range from 30-50 microns.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements (e.g. chambers, sequestration pens and channels) of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, organosilicone, such as polydimethylsiloxane ("PDMS"), or the like), which can be gas permeable. Other examples of materials that can compose microfluidic circuit material 116 include molded glass, a patternable material such as a silicone polymer (e.g. photo-patternable silicone or "PPS"), photo-resist (e.g., an expoxy-based photo-resist such as SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. In some instances, pens 124, 126, 128, 130 are configured to physically corral one or more micro-objects within the microfluidic circuit 120. Sequestration pens in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of a microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
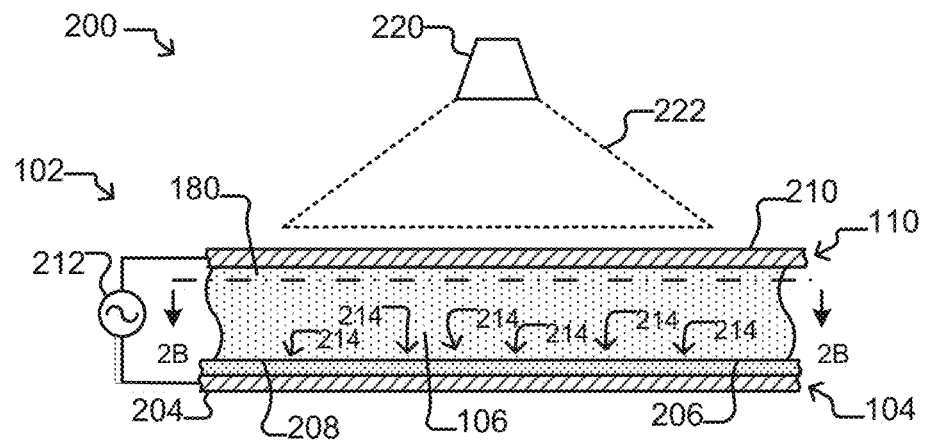
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
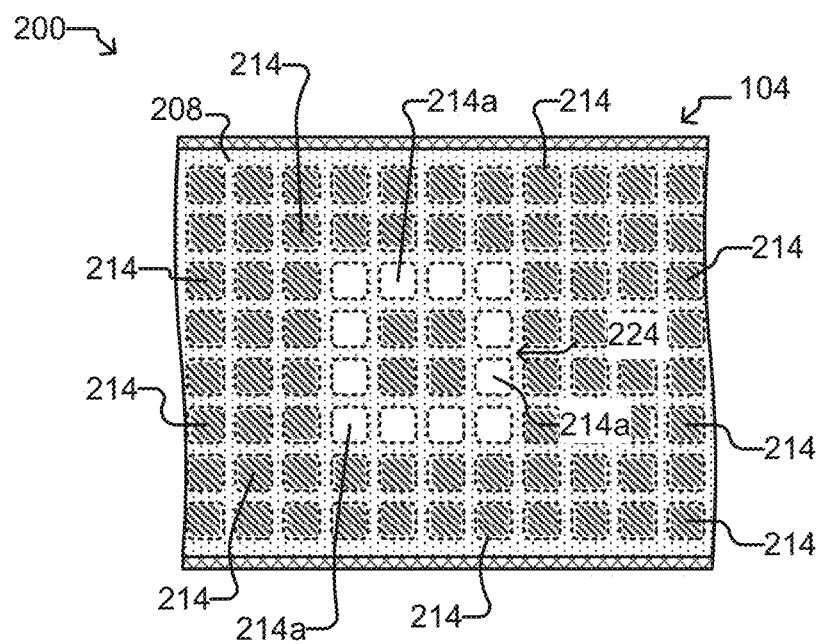

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 75 nm to about 150 nm, or about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the inner surface 208 of the dielectric layer that faces inward toward region/chamber 202 is coated with a hydrophobic coating material (which is sub-group of the materials generally referred to herein as "coating materials"). The hydrophobic coating material can comprise, for example, fluorinated carbon molecules. Examples of fluorinated carbon molecules include perfluoro-polymers such as polytetrafluoroethylene (e.g., TEFLON® or poly(2,3-difluoromethylenyl-perfluorotetrahydrofuran) (e.g., CYTOP™). In other embodiments, the hydrophobic coating material can have a thickness of about 10 nm to about 50 nm.

In some embodiments, molecules that make up the hydrophobic coating material can be covalently bonded to the surface of the dielectric layer. For example, molecules of the hydrophobic coating material can form covalent bonds with the inner surface 208 of the dielectric layer by means of a linking group such as a siloxane group, or a phosphonate ester group. In some embodiments, the hydrophobic coating material can comprise an alkyl group. Thus, in some embodiments, the coating material can comprise alkyl-terminated siloxane or alkyl-terminated phosphonate ester. The alkyl group can comprise carbon atoms that form a linear chain (e.g., a linear chain of at least 10 carbon atoms, or at least 16, 18, 20, 22, or more carbon atoms). The alkyl group can be an unbranched or a branched alkyl group. In some embodiments, the alkyl group can be a substituted alkyl group (e.g., some of the carbons in the alkyl group can be fluorinated or perfluorinated). Accordingly, the coating material can comprise perfluoroalkyl-terminated siloxane or perfluoroalkyl-terminated phosphonate ester. The alkyl group may comprise a linear chain of substituted (e.g., fluorinated or perfluorinated) carbons joined to a linear chain of non-substituted carbons. For example, the alkyl group may include a first segment, which may be a perfluoroalkyl group, joined to a second segment, which may be a non-substituted alkyl group. The first and second segments may be joined directly or indirectly (e.g., by means of an ethereal linkage). The first segment of the alkyl group can be located distal to the linking group, and the second segment of the alkyl group can be located proximal to the linking group. In some embodiments, the coating material may form a monolayer when covalently bound to the surface of the dielectric layer. Thus, for example, the coating material can form a monolayer of perfluoroalkyl-terminated siloxane or perfluoroalkyl-terminated phosphonate ester, which may or may not have an intervening linear chain of non-substituted carbons. In some embodiments, the covalently bonded hydrophobic coating material can have a thickness of less than 10 nm (e.g., less than 5 nm, or about 1.5 to 3.0 nm).

In some embodiments, the inner surface (not shown) of the cover 110 of a microfluidic device 200 having an electrowetting (e.g. OEW) configuration is coated with a coating material (not shown) as well. The hydrophobic coating material can be the same hydrophobic coating material used to coat the inner surface 208 of the dielectric layer, and the hydrophobic coating material can have a thickness that is substantially the same as the thickness of the hydrophobic coating material on the dielectric layer. Moreover, in electrowetting configurations, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In certain embodiments, the hydrophobic coating material is deposited on substantially all exposed regions of the inner surface of the cover 110 and substantially all exposed regions of the inner surface 208 of dielectric layer of the support structure 104 (i.e., on substantially all surfaces facing inward toward the enclosure 102). In some embodiments, the hydrophobic coating material is deposited on all surfaces within the enclosure 102, including on substantially all inner surfaces of microfluidic circuit material 116 used to form circuit elements and structures (e.g. walls forming sequestration pens and chambers) within the enclosure 102.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an oil-based fluid (e.g., a silicone or fluorinated oil) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2C:
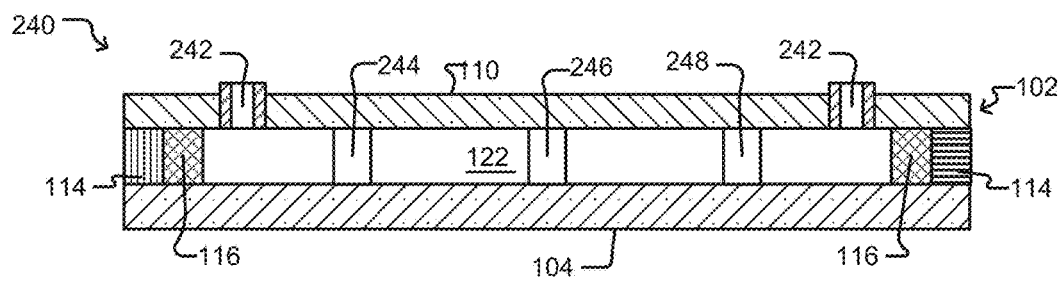
FIGS. 2C and 2D illustrate sequestration pens according to some embodiments of the invention.
Figure 2D:
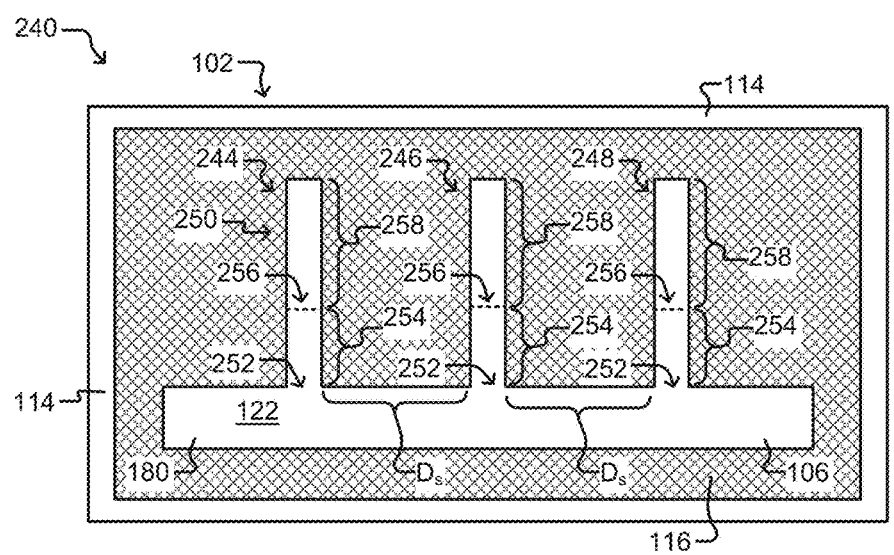

Non-limiting examples of generic sequestration pens 244, 246, and 248 are shown within the microfluidic device 240 depicted in FIGS. 2C and 2D. Each sequestration pen 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the sequestration pen 244, 246, 248 does not extend into the isolation region 258. Thus, due to the connection region 254, a micro-object (not shown) or other material (not shown) disposed in an isolation region 258 of a sequestration pen 244, 246, 248 can thus be isolated from, and not substantially affected by, a flow of medium 180 in the channel 122.

The channel 122 can thus be an example of a swept region, and the isolation regions 258 of the sequestration pens 244, 246, 248 can be examples of unswept regions. As noted, the channel 122 and sequestration pens 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Prior to introduction of the fluidic medium 180, the microfluidic device may be primed with a gas such as carbon dioxide gas. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
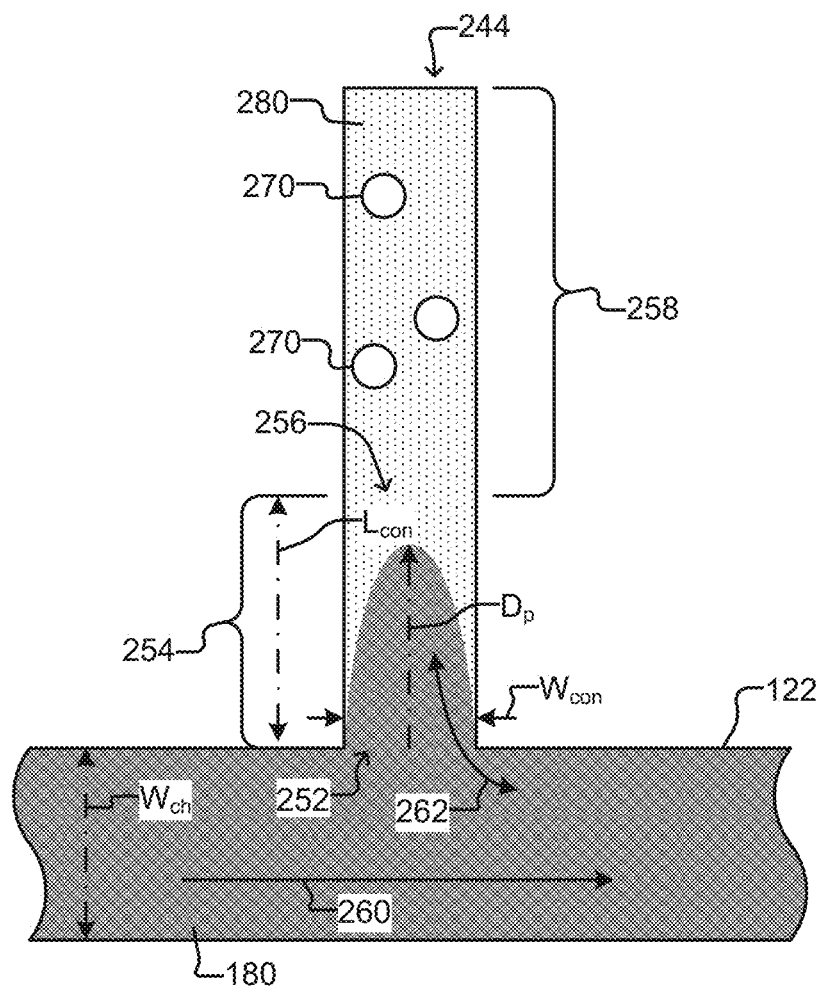
FIG. 2E illustrates a detailed sequestration pen according to some embodiments of the invention.

FIG. 2E illustrates a detailed view of an example of a sequestration pen 244 according to the present invention. Examples of micro-objects 270 are also shown.

As is known, a flow 260 of fluidic medium 180 in a microfluidic channel 122 past a proximal opening 252 of sequestration pen 244 can cause a secondary flow 262 of the medium 180 into and/or out of the sequestration pen 244. To isolate micro-objects 270 in the isolation region 258 of a sequestration pen 244 from the secondary flow 262, the length $L_{con}$ of the connection region 254 of the sequestration pen 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each sequestration pen 244, a maximal velocity $V_{max}$ for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity $V_{max}$, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed $V_{max}$, the flow 260 of fluidic medium 180 in the channel 122 will not move miscellaneous particles (e.g., microparticles and/or nanoparticles) from the channel 122 into the isolation region 258 of a sequestration pen 244. Having the length $L_{con}$ of the connection region 254 be greater than the maximum penetration depth $D_p$ of the secondary flow 262 can thus prevent contamination of one sequestration pen 244 with miscellaneous particles from the channel 122 or another sequestration pen (e.g., sequestration pens 246, 248 in FIG. 2D).

Because the channel 122 and the connection regions 254 of the sequestration pens 244, 246, 248 can be affected by the flow 260 of medium 180 in the channel 122, the channel 122 and connection regions 254 can be deemed swept (or flow) regions of the microfluidic device 240. The isolation regions 258 of the sequestration pens 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and sequestration pens 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and sequestration pens 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

In various embodiments of sequestration pens (e.g. 124, 126, 128, 130, 244, 246 or 248), the isolation region (e.g. 258) is configured to contain a plurality of micro-objects. In other embodiments, the isolation region can be configured to contain only one, two, three, four, five, or a similar relatively small number of micro-objects. Accordingly, the volume of an isolation region can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

In various embodiments of sequestration pens, the width $W_{ch}$ of the channel 122 at a proximal opening (e.g. 252) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a cross-sectional height of about 30 to about 200 microns, or about 50 to about 150 microns. In some embodiments, the sequestration pen has a cross-sectional area of about 100,000 to about 2,500,000 square microns, or about 200,000 to about 2,000,000 square microns. In some embodiments, a connection region has a cross-sectional height that matches the cross-sectional height of the corresponding sequestration pen. In some embodiments, the connection region has a cross-sectional width of about 50 to about 500 microns, or about 100 to about 300 microns.

In various embodiments of sequestration pens the height $H_{ch}$ of the channel 122 at a proximal opening 252 can be within any of the following ranges: 20-150 microns, 20-125 microns, 20-100 microns, 20-80 microns, 20-60 microns, 20-50 microns, 30-150 microns, 30-125 microns, 30-100 microns, 30-80 microns, 30-60 microns, 30-50 microns, 40-150 microns, 40-125 microns, 40-100 microns, 40-80 microns, 40-60 microns, or 40-50 microns. The foregoing are examples only, and the height $H_{ch}$ of the channel 122 can be in other ranges (e.g., a range defined by any of the endpoints listed above). The height $H_{ch}$ of the channel 122 can be selected to be in any of these ranges in regions of the channel other than at a proximal opening of a sequestration pen.

In various embodiments of sequestration pens a cross-sectional area of the channel 122 at a proximal opening 252 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252 can be in other ranges (e.g., a range defined by any of the endpoints listed above).

In various embodiments of sequestration pens, the length $L_{con}$ of the connection region 254 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254 can be in a different ranges than the foregoing examples (e.g., a range defined by any of the endpoints listed above).

In various embodiments of sequestration pens the width $W_{con}$ of a connection region 254 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of f a connection region 254 at a proximal opening 252 can be different than the foregoing examples (e.g., a range defined by any of the endpoints listed above).

In various embodiments of sequestration pens the width $W_{con}$ of a connection region 254 at a proximal opening 252 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254 at a proximal opening 252 can be different than the foregoing examples (e.g., a range defined by any of the endpoints listed above).

In various embodiments of sequestration pens, a ratio of the length $L_{con}$ of a connection region 254 to a width $W_{con}$ of the connection region 254 at the proximal opening 252 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254 at the proximal opening 252 can be different than the forego ng examples.

In various embodiments of microfluidic devices 100, 200, 240, 290, $V_{max}$ can be set around 0.2, 0.3, 0.4, 0.5, 0.6, 0.7, 0.8, 0.9, 1.0, 1.1, 1.2, 1.3, 1.4, or 1.5 µL/sec.

In various embodiments of microfluidic devices having sequestration pens, the volume of an isolation region 258 of a sequestration pen can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more. In various embodiments of microfluidic devices having sequestration pens, the volume of a sequestration pen may be about $5 \times 10^3$, $7 \times 10^3$, $1 \times 10^4$, $3 \times 10^4$, $5 \times 10^4$, $8 \times 10^4$, $1 \times 10^5$, $2 \times 10^5$, $4 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some embodiments, the microfluidic device has sequestration pens wherein no more than $1 \times 10^2$ biological cells may be maintained, and the volume of a sequestration pen may be no more than $2 \times 10^6$ cubic microns. In some embodiments, the microfluidic device has sequestration pens wherein no more than $1 \times 10^2$ biological cells may be maintained, and a sequestration pen may be no more than $4 \times 10^5$ cubic microns. In yet other embodiments, the microfluidic device has sequestration pens wherein no more than 50 biological cells may be maintained, a sequestration pen may be no more than 4×10⁵ cubic microns.

In various embodiment, the microfluidic device has sequestration pens configured as in any of the embodiments discussed herein where the microfluidic device has about 100 to about 500 sequestration pens; about 200 to about 1000 sequestration pens, about 500 to about 1500 sequestration pens, about 1000 to about 2000 sequestration pens, or about 1000 to about 3500 sequestration pens.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens, about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2F:
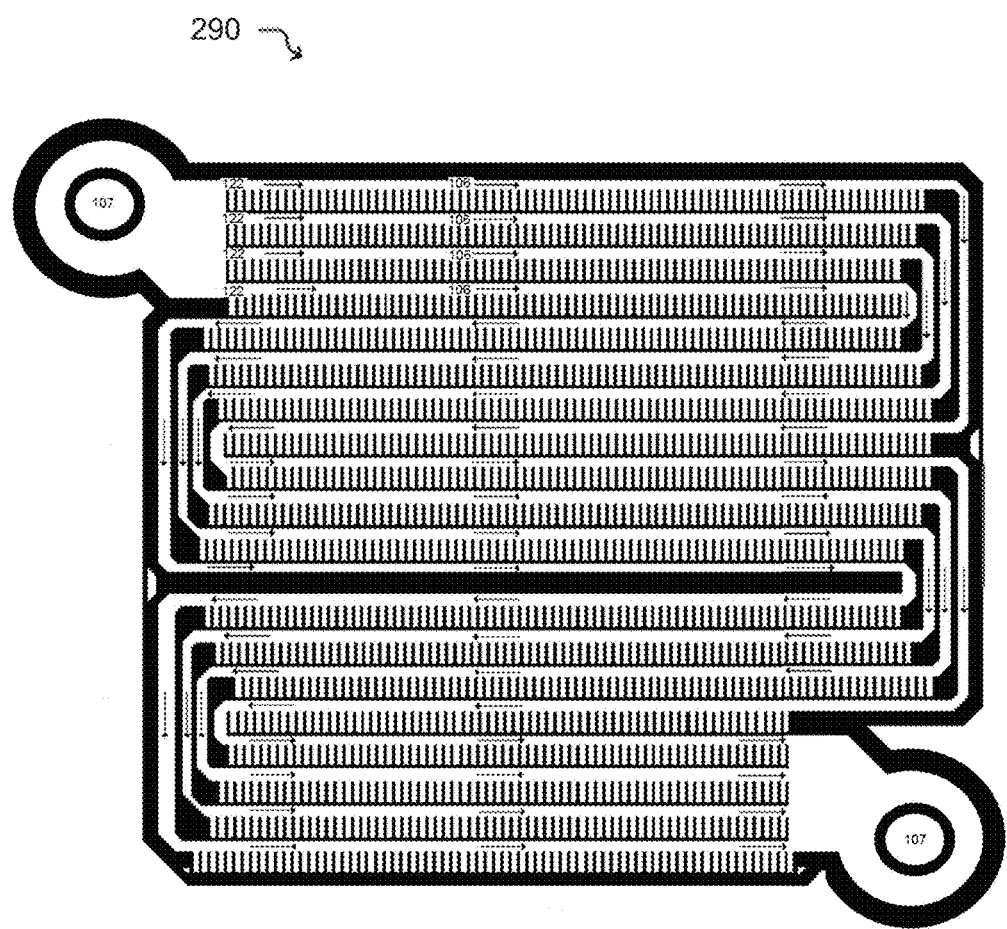
FIG. 2F illustrates a microfluidic device according to an embodiment of the invention.

FIG. 2F illustrates a microfluidic device 290 according to one embodiment. The microfluidic device 290 is illustrated in FIG. 2F is a stylized diagram of a microfluidic device 100. In practice the microfluidic device 290 and its constituent circuit elements (e.g. channels 122 and sequestration pens 128) would have the dimensions discussed herein. The microfluidic circuit 120 illustrated in FIG. 2F has two ports 107, four distinct channels 122 and four distinct flow paths 106. The microfluidic device 290 further comprises a plurality of sequestration pens opening off of each channel 122. In the microfluidic device illustrated in FIG. 2F, the sequestration pens have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
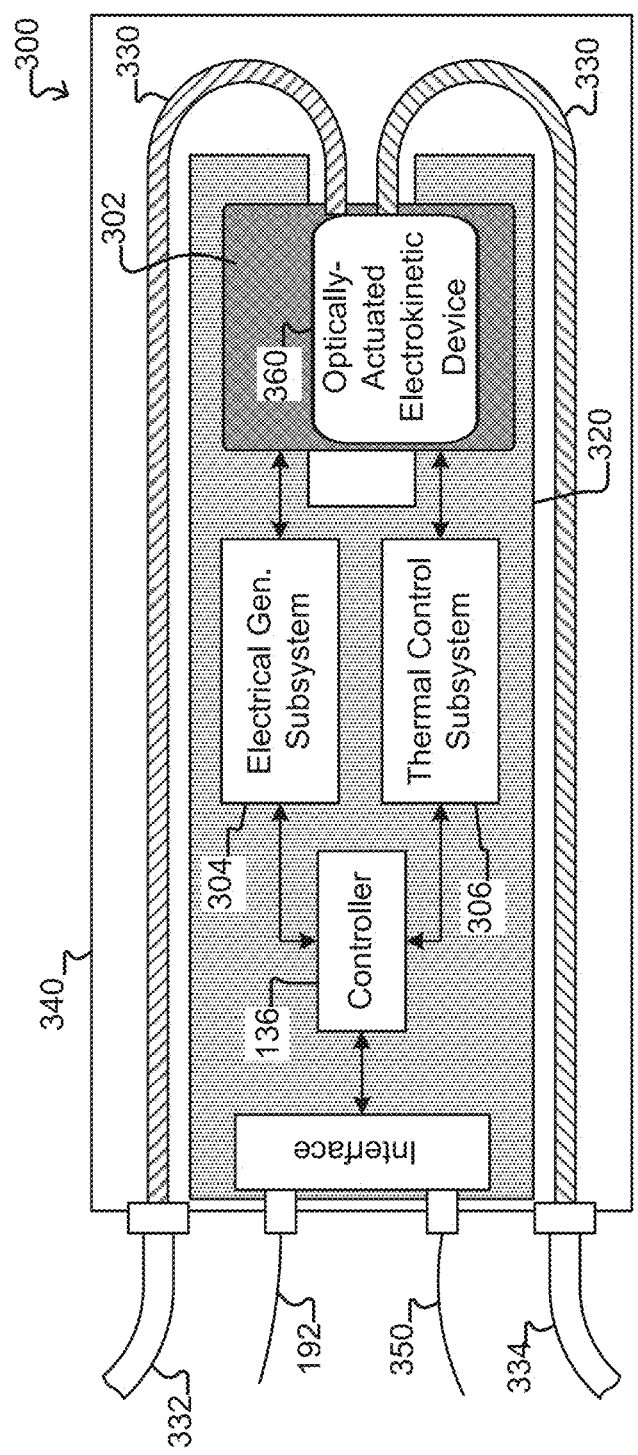
FIG. 3A illustrates a specific example of a system for use with a microfluidic device and associated control equipment according to some embodiments of the invention.
Figure 3B:
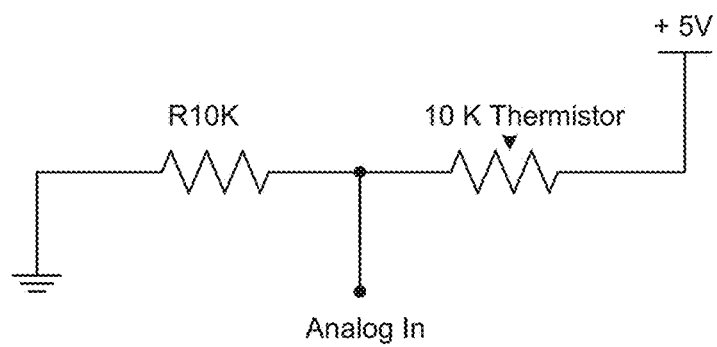
FIG. 3B illustrates an exemplary analog voltage divider circuit according to some embodiments of the invention.

FIGS. 3A through 3D shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electro-wetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary support includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 100.

As illustrated in FIG. 3A, the support structure 300 can further include a thermal control subsystem 306. The thermal control subsystem 306 can be configured to regulate the temperature of microfluidic device 360 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the support structure 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the support structure 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (shown in FIG. 3B) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

Figure 3C:
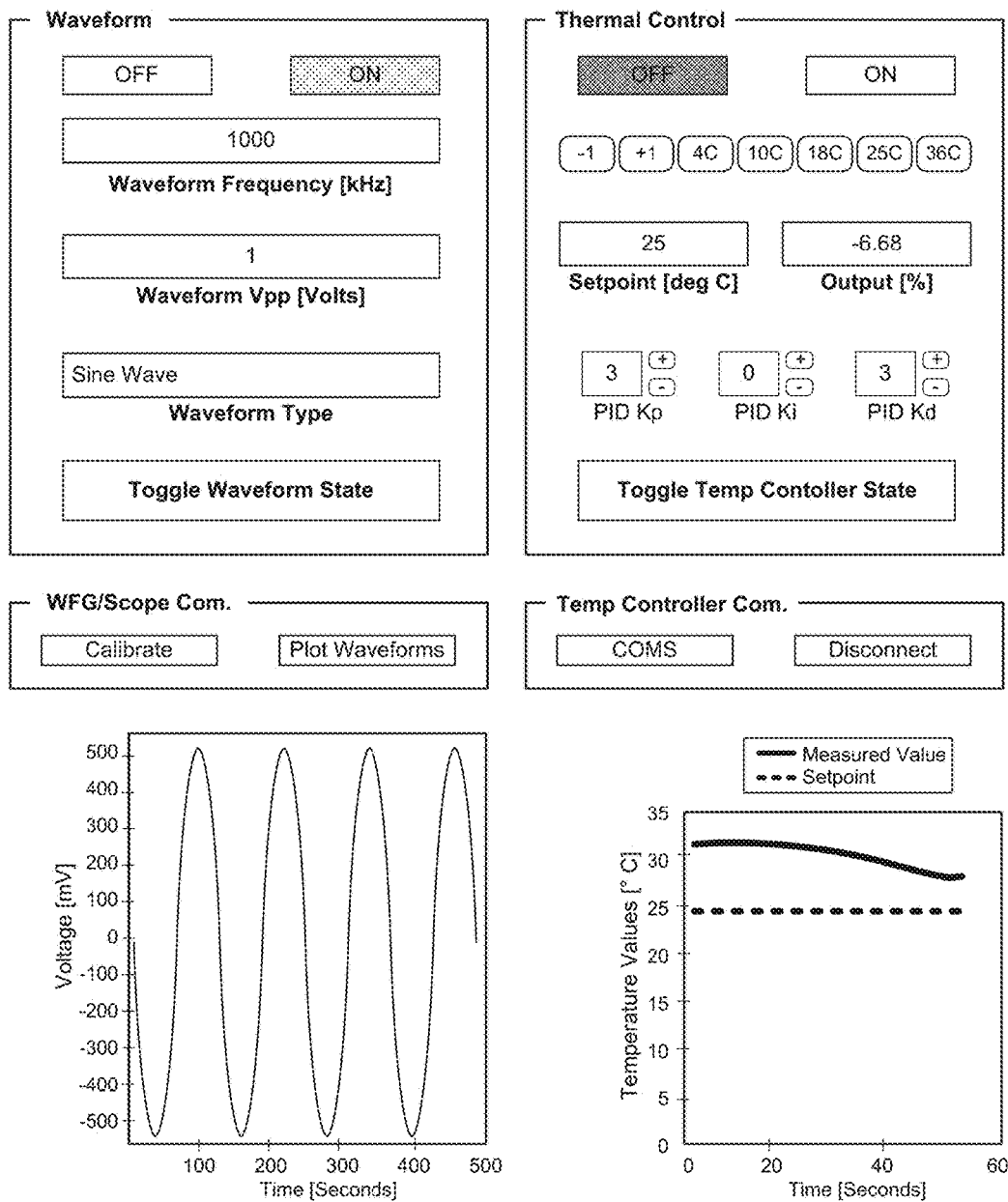
FIG. 3C illustrates an exemplary GUI configured to plot temperature and waveform data according to some embodiments of the invention.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI), one example of which is shown in FIG. 3C, provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 404. The light modulating subsystem 404 can include a digital mirror device (DMD), or a microshutter array system (MSA), either of which can be configured to receive light from a light source 402 and transmits a subset of the received light into an optical train of microscope 400. Alternatively, the light modulating subsystem 404 can include a device that produces its own light (and thus dispenses with the need for a light source 402), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 404 can be, for example, a projector. Thus, the light modulating subsystem 404 can be capable of emitting both structured and unstructured light. One example of a suitable light modulating subsystem 404 is the Mosaic™ system from Andor Technologies™. In certain embodiments, imaging module 164 and/or motive module 162 of system 150 can control the light modulating subsystem 404.

In certain embodiments, the imaging device 194 further comprises a microscope 400. In such embodiments, the nest 300 and light modulating subsystem 404 can be individually configured to be mounted on the microscope 400. The microscope 400 can be, for example, a standard research-grade light microscope or fluorescence microscope. Thus, the nest 300 can be configured to be mounted on the stage 410 of the microscope 400 and/or the light modulating subsystem 404 can be configured to mount on a port of microscope 400. In other embodiments, the nest 300 and the light modulating subsystem 404 described herein can be integral components of microscope 400.

In certain embodiments, the microscope 400 can further include one or more detectors 422. In some embodiments, the detector 422 is controlled by the imaging module 164. The detector 422 can include an eye piece, a charge-coupled device (CCD), a camera (e.g., a digital camera), or any combination thereof. If at least two detectors 422 are present, one detector can be, for example, a fast-frame-rate camera while the other detector can be a high sensitivity camera. Furthermore, the microscope 400 can include an optical train configured to receive reflected and/or emitted light from the microfluidic device 360 and focus at least a portion of the reflected and/or emitted light on the one or more detectors 422. The optical train of the microscope can also include different tube lenses (not shown) for the different detectors, such that the final magnification on each detector can be different.

In certain embodiments, imaging device 194 is configured to use at least two light sources. For example, a first light source 402 can be used to produce structured light (e.g., via the light modulating subsystem 404) and a second light source 432 can be used to provide unstructured light. The first light source 402 can produce structured light for optically-actuated electrokinesis and/or fluorescent excitation, and the second light source 432 can be used to provide bright field illumination. In these embodiments, the motive module 164 can be used to control the first light source 404 and the imaging module 164 can be used to control the second light source 432. The optical train of the microscope 400 can be configured to (1) receive structured light from the light modulating subsystem 404 and focus the structured light on at least a first region in a microfluidic device, such as an optically-actuated electrokinetic device, when the device is being held by the support structure 200, and (2) receive reflected and/or emitted light from the microfluidic device and focus at least a portion of such reflected and/or emitted light onto detector 422. The optical train can be further configured to receive unstructured light from a second light source and focus the unstructured light on at least a second region of the microfluidic device, when the device is held by the support structure 300. In certain embodiments, the first and second regions of the microfluidic device can be overlapping regions. For example, the first region can be a subset of the second region.

Figure 3D:
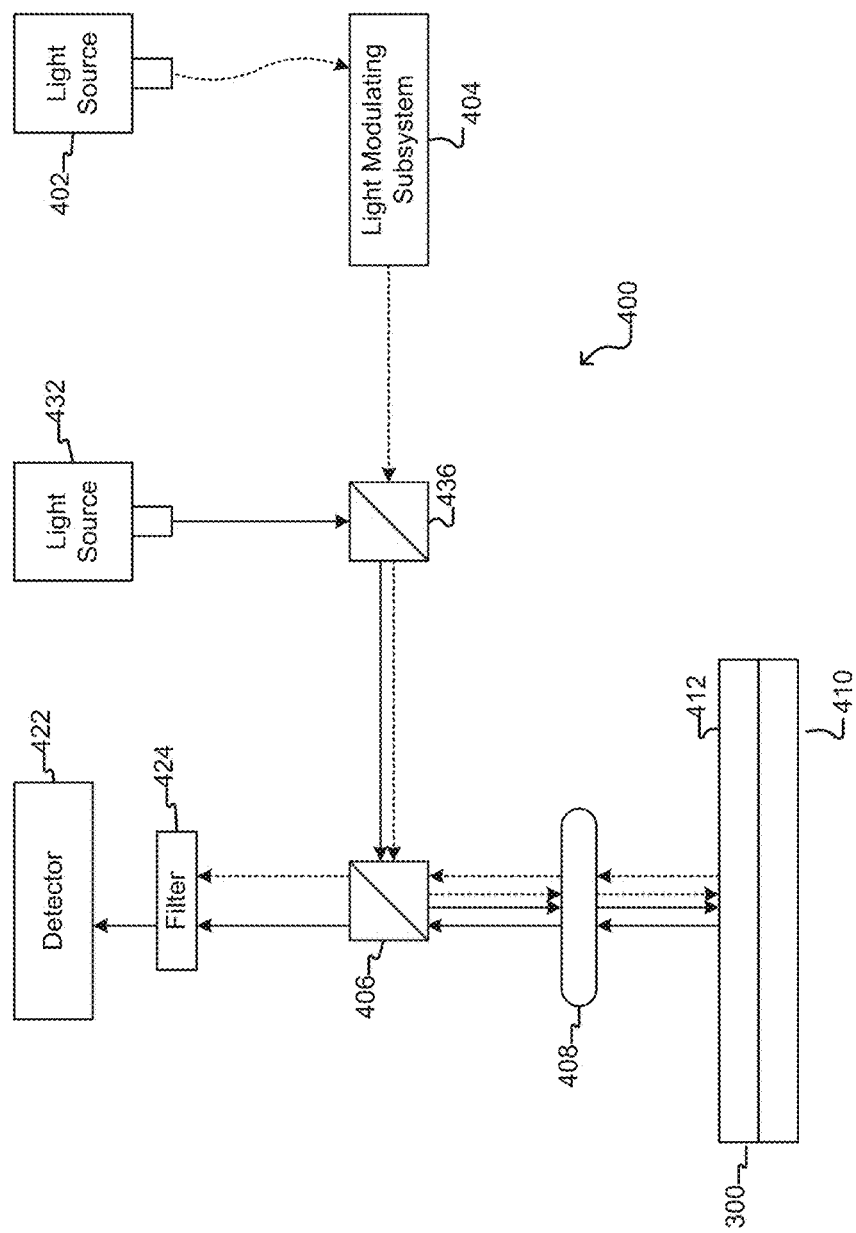
FIG. 3D illustrates an imaging device according to some embodiments of the invention.

In FIG. 3D, the first light source 402 is shown supplying light to a light modulating subsystem 404, which provides structured light to the optical train of the microscope 400. The second light source 432 is shown providing unstructured light to the optical train via a beam splitter 436. Structured light from the light modulating subsystem 404 and unstructured light from the second light source 432 travel from the beam splitter 436 through the optical train together to reach a second beam splitter 436 (or dichroic filter 406, depending on the light provided by the light modulating subsystem 404), where the light gets reflected down through the objective 408 to the sample plane 412. Reflected and/or emitted light from the sample plane 412 then travels back up through the objective 408, through the beam splitter and/or dichroic filter 406, and to a dichroic filter 424. Only a fraction of the light reaching dichroic filter 424 passes through and reaches the detector 422.

In some embodiments, the second light source 432 emits blue light. With an appropriate dichroic filter 424, blue light reflected from the sample plane 412 is able to pass through dichroic filter 424 and reach the detector 422. In contrast, structured light coming from the light modulating subsystem 404 gets reflected from the sample plane 412, but does not pass through the dichroic filter 424. In this example, the dichroic filter 424 is filtering out visible light having a wavelength longer than 495 nm. Such filtering out of the light from the light modulating subsystem 404 would only be complete (as shown) if the light emitted from the light modulating subsystem did not include any wavelengths shorter than 495 nm. In practice, if the light coming from the light modulating subsystem 404 includes wavelengths shorter than 495 nm (e.g., blue wavelengths), then some of the light from the light modulating subsystem would pass through filter 424 to reach the detector 422. In such an embodiment, the filter 424 acts to change the balance between the amount of light that reaches the detector 422 from the first light source 402 and the second light source 432. This can be beneficial if the first light source 402 is significantly stronger than the second light source 432. In other embodiments, the second light source 432 can emit red light, and the dichroic filter 424 can filter out visible light other than red light (e.g., visible light having a wavelength shorter than 650 nm).

Figure 3E:
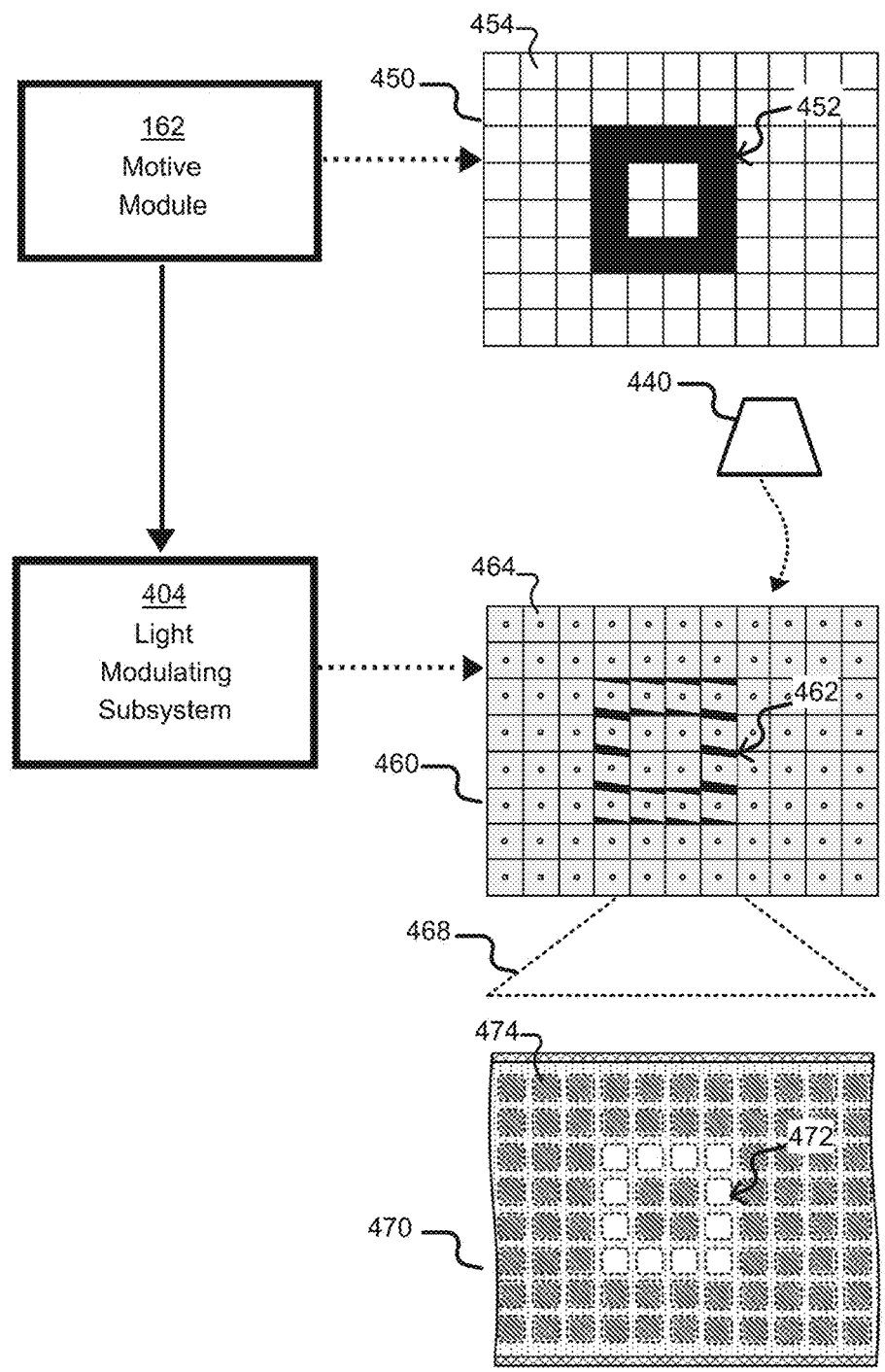
FIG. 3E illustrates the communications between an imaging module and a light modulating subsystem to project patterns of light according to some embodiments of the invention.

FIG. 3E illustrates communications between the motive module 164 and the light modulating subsystem 404 to project patterns of light on a microfluidic device according to a specific embodiment of the invention. As discussed above with respect to FIG. 3D, the light modulating subsystem 404 may comprise an electrically-addressed spatial light modulator and/or an optically-addressed spatial light modulator. Electrically-addressed spatial light modulators comprise an array of individually-addressable spatial light modulators that are controlled by electrodes. In FIG. 3E, the light modulating subsystem 404 is a Digital Mirror Device (DMD) 460 comprising an array of individually-addressable micro-mirrors 464 that are controlled by electrodes. However, in other embodiments, the light modulating subsystem 404 can be a Liquid Crystal on Silicon (LCoS) device comprising an array of individually-addressable electrodes that correspond to pixels in a liquid crystal display.

In the embodiment illustrated in FIG. 3E, the light modulating subsystem 404 uses a separate light source 440 to receive and modulate light. However, in other embodiments, the light modulating subsystem 404 comprises its own light source.

FIG. 3E illustrates communications between the motive module 164 and the light modulating subsystem 404 to project patterns of light on a microfluidic device according to a specific embodiment of the invention. As discussed above with respect to FIG. 3D, the light modulating subsystem 404 may comprise an electrically-addressed spatial light modulator and/or an optically-addressed spatial light modulator. Electrically-addressed spatial light modulators comprise an array of individually-addressable spatial light modulators (i.e. spatial light modulating elements) that are controlled by electrodes. In FIG. 3E, the light modulating subsystem 404 is a Digital Mirror Device (DMD) 460 comprising an array of individually-addressable micro-mirrors 464 that are controlled by electrodes. However, in other embodiments, the light modulating subsystem 404 can be a Liquid Crystal on Silicon (LCoS) device comprising an array of individually-addressable electrodes that correspond to pixels in a liquid crystal display.

In the embodiment illustrated in FIG. 3E, the light modulating subsystem 404 uses a separate light source 440 to receive and modulate light. However, in other embodiments, the light modulating subsystem 404 comprises its own light source.

As illustrated in FIG. 3E, the motive module 162 transmits information 450 specifying a specific pattern of light ("pattern information") to the light modulating subsystem 404. In some embodiments, the pattern information 450 can comprise a bitmap (or similar pixel-based data structure), vector data, or any combination thereof. For purposes of illustration, the pattern information 450 in FIG. 3E is illustrated as a bitmap comprising an array of pixels 454 and including a square pattern 452 of pixels. Depending on the embodiment, the pattern information 450 can be binary (i.e. specify whether or not to project a pattern of light) or contain values indicating an intensity of light to project. In instances where the spatial light modulators are micro-mirrors 464, the micro-mirrors 464 may create different intensities of light by rapidly switching the mirrors between an "on" and "off" state (i.e. "dithering" the micro-mirrors).

The light modulating subsystem 404 receives the pattern information 450 from the motive module 162 and uses the pattern information 450 to direct the projection of a pattern of light 468 onto DEP electrode regions 474 on the microfluidic device 470. In the embodiment illustrated in FIG. 3E, a DMD 460 rotates a plurality 462 of individually-addressable micro-mirrors 464 corresponding to the square pattern information 450 into an "on state." The square pattern of individual-addressable micro-mirrors 462 modulates the light from the light source 440 to project a pattern of light 468 onto the microfluidic device 470 that illuminates a square pattern of DEP electrode regions 472 in the array of DEP electrode regions 474 in the microfluidic device 470.

In some embodiments, there is a one-to-one correspondence between the array of individually-addressable spatial light modulating elements 464 that project light onto the microfluidic device 470 and the array of DEP electrode regions 474 in the microfluidic device 470. In this way, each individually-addressable spatial light modulating element 464 can project light to generate light-actuated DEP force at a corresponding DEP electrode region 474. In these embodiments, the motive module 162 can send pattern information 450 to the light modulating subsystem 404 that specifies the DEP electrode regions 474 to project light onto. For example, instead of sending bitmap and or vector data to the light modulating subsystem 404, the motive module 162 can communicate directly with the individually-addressable spatial light modulators to control which of the DEP electrode regions 474 are illuminated on the microfluidic device 470. Once illuminated the DEP electrode regions 474 may exert OET or OEW force on surrounding micro-objects.

As discussed above, in some embodiments, the spatial light modulating elements 464 can receive pattern information 450 specifying an intensity of light to project. In a specific embodiment, the pattern information 450 may specify a gradation of light to project over adjacent DEP electrode regions 474 in the microfluidic device. In some embodiments, the pattern information 450 may specify a gradation of light that decreases in intensity over adjacent DEP electrode regions 474. For example, the pattern information 450 may specify that about 100% of the maximum light intensity is to be projected at a first DEP electrode region 474, that 70% of the maximum light intensity is to be projected at a second DEP electrode region 474 adjacent to the first DEP electrode region 474, and that 10% of the maximum light intensity is to be projected at a third DEP electrode region 474 adjacent to the second DEP electrode region 474. Various combinations of light intensities may be used to project a gradation over various numbers of DEP electrode regions 474 (e.g. any decreasing combination of about 100%, about 90%, about 80%, about 70%, about 60%, about 50%, about 40%, about 30%, about 20%, and about 10%, and any values therebetween, of the maximum light intensity over any number of DEP electrode regions 474). Similarly, the pattern information 450 may specify a gradation of light that increases in intensity over any number of DEP electrode regions 474 or a gradation of light that both increases and decreases in intensity over any number of DEP electrode regions 474.

Microfluidic Devices and Systems Including Same

Aspects of the present disclosure are drawn to methods of isolating a cell nucleus using a microfluidic device, e.g., a microfluidic device as disclosed herein. The isolated cell nucleus (or multiple isolated cell nuclei) can be analyzed, processed, or further manipulated as desired. Such downstream actions may be performed within the microfluidic device or may be performed once the isolated cell nucleus is exported or otherwise harvested from the microfluidic device.

In certain embodiments, a cell nucleus isolation method includes introducing a cell nucleus (or one or more cell nuclei) into a microfluidic device having a substrate configured to selectively generate forces that move micro-objects and then moving the cell nucleus to a desired location in the microfluidic device, thus isolating the cell nucleus. The cell nucleus is generally introduced into the microfluidic device in a fluid medium that preserves the integrity of the cell nucleus and is amenable for use in the microfluidic device for subsequent cell nucleus movement/isolation. Introducing the cell nucleus into the microfluidic device can be achieved by flowing a medium containing the cell nucleus into a flow region of the microfluidic device which is in fluid connection with at least one isolation region and moving said cell nucleus from the flow region to the isolation region. The flow region of the microfluidic device can include a flow channel (e.g., flow channel 122 of FIGS. 1, 2E and 2F), to which the isolation region is most immediately connected. The isolation region can be present in a sequestration pen of the microfluidic device (e.g., isolation regions 258 in sequestration pens 244, 246, and 248 of FIG. 2D). The flow region (or flow channel) and the isolation region of the microfluidic device are configured such that the flow of medium/fluid through the flow region does not penetrate into the isolation region. Examples of microfluidic devices having such a configuration of are described in detail above (see e.g., FIGS. 2D, 2E and 2F, and descriptions thereof). In certain embodiments, cell nuclei are introduced into the flow region of a microfluidic device through a port (e.g., port 107 in FIG. 1) comprising a passage into the enclosure 102. Introducing cell nuclei into the microfluidic device is referred to herein as "loading" the nuclei onto the microfluidic device.

Once the cell nucleus/nuclei are in the flow region, the microfluidic device is controlled or manipulated, e.g., using the control module and control/monitoring equipment, to move the cell nucleus from the flow region to the first isolation region through selective application of one or more forces. Any of a number of different forces may be used alone or in combination to move a cell nucleus, including gravity, centrifugal force, magnetic force, fluid flow, or DEP forces (as detailed above). As such, in certain embodiments, moving said cell nucleus from the flow region to an isolation region comprises manipulating the micro-fluidic device such that a gravitational force acts upon the cell nucleus and moves it in a desired direction, e.g., pulls it into or toward the isolation region. Manipulating the microfluidic device may include tilting the device to impart the desired gravitational force. Centrifugal forces can be applied by rotating or centrifuging the device, while fluid can be flowed through swept regions of the device to move a cell nucleus, e.g., flowing from an inlet port to a flow channel or from a flow channel to an outlet port.

In certain embodiments, DEP forces, such as OET forces, are used to move a cell nucleus to an isolation region in the microfluidic device. As described above, moving a cell nucleus thus can include generating DEP forces that direct a cell nucleus along a desired or pre-determined path, e.g., from a channel to an isolation region of a sequestration pen. The DEP forces may attract or repel the cell nucleus to achieve movement along the desired path. Generating DEP forces in the microfluidic device includes activating (e.g., optically activating) DEP electrodes located at the surface of the substrate of the microfluidic device. For example, the substrate of the microfluidic device can include a layer of amorphous silicon that exhibits increased conductivity at a desired position(s) by directing light to the position(s) on the substrate (e.g., visible light). In such embodiments, the DEP electrodes are referred to as virtual electrodes (as described in U.S. Pat. No. 7,612,355 (now RE 44,711)). In additional embodiments, DEP electrodes can be phototransistors (e.g., as described in U.S. Pat. No. 7,956,339). DEP electrodes may be controlled by a photo-actuated transistor (e.g., a CMOS chip design as described in US2014/0124370) or by an electrically-actuated transistor (e.g., as described in U.S. Pat. No. 6,942,776). In many embodiments, each DEP electrode is controlled independently of the other DEP electrodes.

In certain embodiments, EW forces, such as OEW forces, are used to move an aqueous droplet containing a cell nucleus to an isolation region in the microfluidic device. As described above, moving a cell nucleus thus can include generating EW forces that direct the droplet and a cell nucleus contained therein along a desired or pre-determined path, e.g., from a channel to an isolation region of a sequestration pen. The EW forces may attract the aqueous droplet (and cell nucleus) by creating a relative electrostatic attraction with the leading edge of the droplet to achieve movement along the desired path. Generating EW forces in the microfluidic device includes activating (e.g., optically activating) EW electrodes located beneath the dielectric layer of the substrate of the microfluidic device. For example, the substrate of the microfluidic device can include a layer of amorphous silicon that exhibits increased conductivity at a desired position(s) by directing light to the position(s) on the substrate (e.g., visible light). In such embodiments, the EW electrodes can be referred to as virtual electrodes, as described in U.S. Pat. No. 6,958,132 (Chiou et al.). Alternatively, the microfluidic device can have an EWOD configuration with selectively addressable and energizable electrodes, as described in U.S. Pat. No. 8,685,344 (Sundarsan et al.).

Blocking Solutions and Blocking Agents.

Without intending to be limited by theory, after cells are lysed to release nuclei, the remaining nuclei may have excess matter (e.g. proteins and/or nucleic acid in the cytoplasm of the cell) present on the membranes of the nuclei that cause the nuclei to adhere or "stick" to the inner surfaces of the microfluidic device. In some embodiments, one or more of the inner surfaces of the microfluidic device (e.g. the inner surface of the cover of the microfluidic device or the electrode activation substrate of the microfluidic device), are treated with a blocking solution and/or blocking agent to prevent or reduce nuclei adherence. In some embodiments, the cell nuclei are imported in a blocking solution that includes one or more blocking agents.

In other embodiments, the inner surface(s) of the microfluidic device (e.g., a DEP-configured microfluidic device) are pre-treated or "primed" with a blocking solution comprising a blocking agent prior to introduction of the cell nuclei. Any convenient blocking agent/blocking solution can be used, including but not limited to: serum or serum factors, bovine serum albumin (BSA), polymers, detergents, enzymes, and any combination thereof. In some specific embodiments, a blocking agent will be used to treat the inner surface(s) of the microfluidic device. In one example, a polymer comprising alkylene ether moieties can be included as a blocking agent in the blocking solution. A wide variety of alkylene ether containing polymers may be suitable. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a conditioned surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. In another example, DNase can be included in the blocking agent in a blocking solution to remove extranuclear DNA that might cause sticking to the substrate and/or walls of the microfluidic device.

In some embodiments, a blocking solution can comprise various proteins and/or peptides as blocking agents. In a specific embodiment, a blocking solution that finds use in the present disclosure includes a protein such as albumin (e.g. BSA) and/or serum (or a combination of multiple different sera) comprising albumin and/or one or more other similar proteins as blocking agents. The serum can be from any convenient source, including but not limited to fetal calf serum, sheep serum, goat serum, horse serum, and the like. In certain embodiments, BSA in a blocking solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a blocking solution is present in a range of from about 20% (v/v) to about 50% v/v, including 25%, 30%, 35%, 40%, 45%, or more or anywhere in between. In some embodiments, BSA is present as a blocking agent in a blocking solution at 5 mg/mL, whereas in other embodiments, BSA is present as a blocking agent in a blocking solution at 70 mg/mL. In certain embodiments, serum is present as a blocking agent in a blocking solution at 30%.

Coating Materials.

Depending on the embodiment, any of the foregoing blocking agents/blocking solutions can be replaced by or used in combination with various coating materials used to coat one or more of the inner surface(s) of the microfluidic device (e.g., a DEP-configured and/or EW-configured microfluidic device). In some embodiments, at least one surface of the microfluidic device includes a coating material that reducing surface fouling and/or prevents or reduces nuclei from sticking to the surface. In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Polymer-Based Coating Materials.

The at least one inner surface may include a coating material that comprises a polymer. The polymer may be covalently or non-covalently bound (or linked) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA).

In other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. These latter exemplary polymers are polyelectrolytes and may alter the characteristics of the surface to deter nuclei sticking.

In some embodiments, the coating material may include a polymer containing urethane moieties, such as, but not limited to polyurethane.

In other embodiments, the coating material may include a polymer containing phosphate moieties, either at a terminus of the polymer backbone or pendant from the backbone of the polymer.

In other embodiments, the coating material may include a polymer containing saccharide moieties. In a non-limiting example, polysaccharides such as those derived from algal or fungal polysaccharides such as xanthan gum or dextran may be suitable to form a material which may reduce or prevent nucleic sticking in the microfluidic device. For example, a dextran polymer having a size about 3 Kda may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation. A nucleic acid containing polymer may include a polyelectrolyte which may reduce or prevent nuclei sticking.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA). In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In further embodiments, the coating material may include a polymer including amine moieties. The polyamino polymer may include a natural polyamine polymer or a synthetic polyamine polymer. Examples of natural polyamines include spermine, spermidine, and putrescine.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that reduce surface fouling and/or prevent or reduce nuclei sticking to the surface the microfluidic device. The covalently linked molecules include a linking group, wherein the linking group is covalently linked to a surface of the microfluidic device. The linking group is also covalently linked to a moiety configured to reduce surface fouling and/or prevent or reduce nuclei sticking to the surface the microfluidic device. The surface to which the linking group links may include a surface of the substrate of the microfluidic device which, for embodiments in which the microfluidic device includes a DEP configuration, can include silicon and/or silicon dioxide. In some embodiments, the covalently linked coating materials coat substantially all of the inner surfaces of the microfluidic device.

In some embodiments, the covalently linked moiety configured to reduce surface fouling and/or prevent or reduce nuclei sticking to the surface the microfluidic device may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The covalently linked moiety configured to reduce surface fouling and/or prevent or reduce nuclei sticking to the surface the microfluidic device may be any polymer as described herein, and may include one or more polymers containing alkylene oxide moieties, carboxylic acid moieties, saccharide moieties, sulfonic acid moieties, phosphate moieties, amino acid moieties, nucleic acid moieties, or amino moieties.

In other embodiments, the covalently linked moiety configured to reduce surface fouling and/or prevent or reduce nuclei sticking to the surface the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety.

In some embodiments, the covalently linked moiety may be an alkyl group that comprises carbon atoms that form a linear chain (e.g., a linear chain of at least 10 carbons, or at least 14, 16, 18, 20, 22, or more carbons). Thus, the alkyl group may be an unbranched alkyl. In some embodiments, the alkyl group may include a substituted alkyl group (e.g., some of the carbons in the alkyl group can be fluorinated or perfluorinated). The alkyl group may comprise a linear chain of substituted (e.g., fluorinated or perfluorinated) carbons joined to a linear chain of non-substituted carbons. For example, the alkyl group may include a first segment, which may include a perfluoroalkyl group, joined to a second segment, which may include a non-substituted alkyl group. The first and second segments may be joined directly or indirectly (e.g., by means of an ether linkage). The first segment of the alkyl group may be located distal to the linking group, and the second segment of the alkyl group may be located proximal to the linking group. In other embodiment, the alkyl group may include a branched alkyl group and may further have one or more arylene group interrupting the alkyl backbone of the alkyl group. In some embodiments, a branched or arylene-interrupted portion of the alkyl or fluorinated alkyl group is located at a point distal to the linking group and the covalent linkage to the surface.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having covalently charged moieties attached to an alkyl or fluoroalkyl chain having a greater number of methylene or fluoromethylene units. In some embodiments, the coating material having more than one kind of covalently linked moiety may be designed such that a first set of molecules which have a greater number of backbone atoms, and thus a greater length from the covalent attachment to the surface, may provide capacity to present bulkier moieties at the coated surface, while a second set of molecules having different, less sterically demanding termini and fewer backbone atoms can help to functionalize the entire substrate surface and thereby prevent undesired adhesion or contact with silicon or alumina making up the substrate itself. In another example, the covalently linked moieties may provide a zwitterionic surface presenting alternating charges in a random fashion on the surface.

Conditioned Surface Properties.

In some embodiments, the covalently linked moieties may form a monolayer when covalently linked to the surface of the microfluidic device (e.g., a DEP configured substrate surface). In some embodiments, the conditioned surface formed by the covalently linked moieties may have a thickness of less than 10 nm (e.g., less than 5 nm, or about 1.5 to 3.0 nm). In other embodiments, the conditioned surface formed by the covalently linked moieties may have a thickness of about 10 nm to about 50 nm. In some embodiments, the conditioned surface does not require a perfectly formed monolayer to be suitably functional for operation within a DEP-configured microfluidic device.

In various embodiments, the coating material of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

Aside from the composition of the coating material, other factors such as physical (and electrical) thickness of the coating material can impact the generation of DEP force and/or electrowetting force by a substrate in a microfluidic device. Various factors can alter the physical and electrical thickness of the coating material, including the manner in which the coating material is deposited on the substrate (e.g. vapor deposition, liquid phase deposition, spin coating, or electrostatic coating). The physical thickness and uniformity of the coating material can be measured using an ellipsometer.

Besides their electrical properties, the coating material may have properties that are beneficial in use with biological molecules. For example, coating materials that contain fluorinated (or perfluorinated) alkyl groups may provide a benefit relative to unsubstituted alkyl groups in reducing the amount of surface fouling. Surface fouling, as used herein, refers to the amount of material indiscriminately deposited on the surface of the microfluidic device, which may include permanent or semi-permanent deposition of biomaterials such as protein and degradation products, nucleic acids, and respective degradation products. Such fouling can increase the amount of adhesion of biological micro-objects to the surface.

Various electrical and functional properties for different coating materials that can be used in microfluidic devices are included in the table below.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). The physical thickness and uniformity of the conditioned surface can be measured using an ellipsometer.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Various properties for conditioned surfaces which may be used in DEP configurations are included in the table below. As can be seen, for entries 1 to 7, which were all covalently linked conditioned surfaces as described herein, the thickness as measured by ellipsometry were consistently thinner than that of entry 8, a CYTOP surface which was formed by non-covalent spin coating (N/A represents data not available throughout the table). Fouling was found to be more dependent upon the chemical nature of the surface than upon the mode of formation as the fluorinated surfaces were typically less fouling than that of alkyl (hydrocarbon) conditioned surfaces.

TABLE 1

Properties of various conditioned surfaces prepared by covalently modifying a surface, compared to CYTOP, a non-covalently formed surface.

| Surface modification type | Formula of surface modifying reagent | Thickness | Fouling |
|---|---|---|---|
| Alkyl terminated siloxane ($C_{16}$) | $CH_3$—$(CH_2)_{15}$—Si—$(OCH_3)3$ | N/A | More fouling than fluorinated layers. |
| Alkyl terminated siloxane ($C_{18}$) | $CH_3$—$(CH_2)_{17}$—Si—$(OCH_3)_3$ | ~2 nm | More fouling than fluorinated layers. |
| Alkyl-terminated phosphonate ester $C_{18}PA$ | $CH_3$—$(CH_2)_{17}$—P=O(OH)2 | N/A | More fouling than fluorinated layers. |
| Alkyl terminated siloxane ($C_{22}$) | $CH_3$—$(CH_2)_{21}$—Si—$(OCH_2CH_3)_3$ | ~2-2.5 nm | More fouling than fluorinated layers. |
| Fluoro-alkyl-terminated alkyl-siloxane $C_{10}F$ | $CF_3$—$(CF_2)_7$—$(CH_2)_2$—Si—$(OCH_3)_3$ | ~1 nm | More resistant to fouling than alkyl-terminated layers |
| Fluoro-alkyl-terminated alkyl-siloxane ($C_{16}F$) | $CF_3$—$(CF_2)_{13}$—$(CH_2)_2$—Si—$(OCH_3)_3$ | ~2 nm | More resistant to fouling than alkyl-terminated layers |
| Fluoro-alkyl-terminated alkoxy-alkyl-siloxane $C_6FC_{13}$ | $CF_3$—$(CF_2)_5$—$(CH_2)_2$—O—$(CH_2)_{11}$—$Si(OCH_3)_3$ | ~2 nm | N/A |
| CYTOP Fluoropolymer [1,2] | | ~30 nm | More resistant to fouling than alkyl-terminated layers |

[1] CYTOP structure:

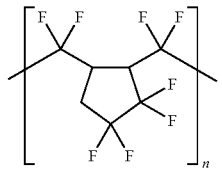

[2] Spin coated, not covalent.

Linking Group to Surface.

The covalently linked moieties forming the coating material are attached to the surface via a linking group. The linking group may be a siloxy linking group formed by the reaction of a siloxane-containing reagent with oxides of the substrate surface, which can include silicon oxide (e.g., for a DEP-configured substrate) or aluminum oxide or hafnium oxide (e.g., for a EW-configured substrate). In some other embodiments, the linking group may be a phosphonate ester formed by the reaction of a phosphonic acid containing reagent with the oxides of the substrate surface.

Multi-Part Conditioned Surface.

The covalently linked coating material may be formed by reaction of a molecule which already contains the moiety configured to reduce surface fouling and/or prevent or reduce nuclei sticking to the surface the microfluidic device (e.g., an alkyl siloxane reagent or a fluoro-substituted alkyl siloxane reagent, which may include a perfluoroalkyl siloxane reagent), as is described below. Alternatively, the covalently linked coating material may be formed by coupling the moiety configured to reduce surface fouling and/or prevent or reduce nuclei sticking to a surface modifying ligand that itself is covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1.

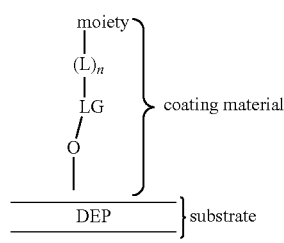

Formula 1

The coating material may be linked covalently to oxides of the surface of a DEP-configured substrate. The DEP-configured substrate may comprise silicon or alumina or hafnium oxide, and oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to reduce surface fouling and/or prevent or reduce nuclei sticking to the surface the microfluidic device can be any of the moieties described herein. The linking group LG may be directly or indirectly connected to the moiety configured to reduce surface fouling and/or prevent or reduce nuclei sticking to the surface the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, in some non-limiting examples. Additionally, the linker L may have one or more arylene, heteroarylene, or heterocyclic groups interrupting the backbone of the linker. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety configured to reduce surface fouling and/or prevent or reduce nuclei sticking to the surface the microfluidic device is added to the surface of the substrate in a one step process, a molecule of Formula 2 may be used to introduce the coating material:

moiety-(L)n-LG.         Formula 2

In some embodiments, the moiety configured to reduce surface fouling and/or prevent or reduce nuclei sticking to the surface the microfluidic device may be added to the surface of the substrate in a multi-step process. When the moiety configured to reduce surface fouling and/or prevent or reduce nuclei sticking is coupled to the surface in a step wise fashion, the linker L may further include a coupling group CG, as shown in Formula 3.

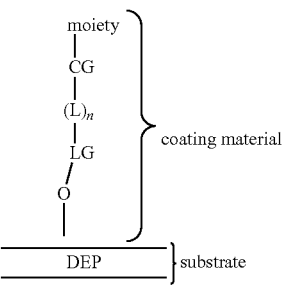

Formula 3

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to reduce surface fouling and/or prevent or reduce nuclei sticking to the surface the microfluidic device) of a linker L. In some other embodiments, the coupling group CG may interrupt the backbone of the linker L. In some embodiments, the coupling group CG is triazolylene, which is the result of a reaction between an alkyne group and an azide group, either of which may be the reactive moiety $R_x$ or the reactive pairing moiety $R_{px}$, as is known in the art for use in Click coupling reactions. A triazolylene group may also be further substituted. For example, a dibenzocylcooctenyl fused triazolylene group may result from the reaction of a moiety bound to a dibenzocyclooctynyl reactive pairing moiety $R_{px}$ with an azido reactive moiety $R_x$ of the surface modifying molecule, which are described in more detail in the following paragraphs. A variety of dibenzocyclooctynyl modified molecules are known in the art or may be synthesized to incorporate a moiety configured to support cell growth, viability, portability, or any combination thereof.

When the coating material is formed in a multi-step process, the moiety configured to reduce surface fouling and/or prevent or reduce nuclei sticking to the surface the microfluidic device may be introduced by reaction of a moiety-containing reagent (Formula 5) with a substrate having a surface modifying ligand covalently linked thereto (Formula 6).

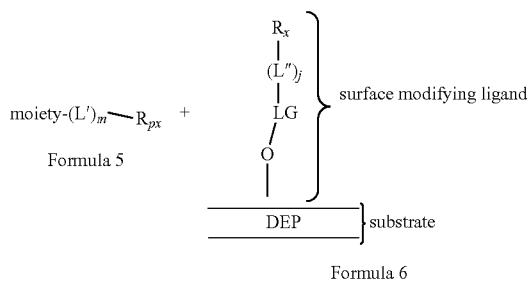

Formula 5 / Formula 6

The modified surface of Formula 4 has a surface modifying ligand attached thereto, which has a formula of -LG-(L")j-$R_x$, which is linked to the oxide of the substrate and is formed similarly as described above for the conditioned surface of Formula 1. The surface of the substrate can be a DEP-configured substrate surface as described above, and can include oxides either native to the substrate or introduced therein. The linking group LG is as described above. A linker L" may be present (j=1) or absent (j=0). The linker L" may have a linear portion where a backbone of the linear portion may include 1 to 100 non-hydrogen atoms selected from of any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker. In some embodiments, the backbone of the linker L" may include 10 to 20 carbon atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

A reactive moiety $R_x$ is present at the terminus of the surface modifying ligand distal to the covalent linkage of the surface modifying ligand with the surface. The reactive moiety $R_x$ is any suitable reactive moiety useful for coupling reactions to introduce the moiety configured to reduce surface fouling and/or prevent or reduce nuclei sticking to the surface the microfluidic device. In some embodiments, the reactive moiety $R_x$ may be an azido, amino, bromo, a thiol, an activated ester, a succinimidyl or alkynyl moiety.

Moiety-Containing Reagent.

The moiety-containing reagent (Formula 5) is configured to supply the moiety configured to reduce surface fouling and/or prevent or reduce nuclei sticking to the surface the microfluidic device.

Moiety-(L')$_m$-$R_{px}$    Formula 5

The moiety configured to reduce surface fouling and/or prevent or reduce nuclei sticking to the surface the microfluidic device of the moiety-containing reagent is linked to the surface modifying ligand by reaction of a reactive pairing moiety $R_{px}$ with the reactive moiety $R_x$. The reactive pairing moiety $R_{px}$ is any suitable reactive group configured to react with the respective reactive moiety $R_x$. In one non-limiting example, one suitable reactive pairing moiety $R_{px}$ may be an alkyne and the reactive moiety $R_x$ may be an azide. The reactive pairing moiety $R_{px}$ may alternatively be an azide moiety and the respective reactive moiety $R_x$ may be alkyne. In other embodiments, the reactive pairing moiety $R_{px}$ may be an active ester functionality and the reactive moiety $R_x$ may be an amino group. In other embodiments, the reactive pairing moiety $R_{px}$ may be aldehyde and the reactive moiety $R_x$ may be amino. Other reactive moiety-reactive pairing moiety combinations are possible, and these examples are in no way limiting.

The moiety configured to reduce surface fouling and/or prevent or reduce nuclei sticking to the surface the microfluidic device of the moiety-containing reagent of Formula 5 may include any of the moieties described herein, including alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The moiety configured to reduce surface fouling and/or prevent or reduce nuclei sticking to the surface the microfluidic device of the moiety-containing reagent of Formula 5 may be directly connected (i.e., L', where m=0) or indirectly connected to the reactive pairing moiety $R_{px}$. When the reactive pairing moiety $R_{px}$ is connected indirectly to the moiety configured to reduce surface fouling and/or prevent or reduce nuclei sticking, the reactive pairing moiety $R_{px}$ may be connected to a linker L' (m=1). The reactive pairing moiety $R_{px}$ may be connected to a first end of the linker L', and the moiety configured to reduce surface fouling and/or prevent or reduce nuclei sticking may be connected to a second end of the linker L'. Linker L' may have a linear portion wherein a backbone of the linear portion includes 1 to 100 non-hydrogen atoms selected from of any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L' may have one or more arylene, heteroarylene, or heterocyclic groups interrupting the backbone of the linker L'. In some embodiments, the backbone of the linker L' may include 10 to 20 atoms. In other embodiments, the backbone of the linker L' may include about 5 atoms to about 100 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety-containing reagent (Formula 5) reacts with the surface having a surface modifying ligand (Formula 3), a substrate having a conditioned surface of Formula 2 is formed. Linker L' and linker L" then are formally part of linker L, and the reaction of the reactive pairing moiety $R_{px}$ with the reactive moiety $R_x$ yields the coupling group CG of Formula 2.

Surface Modifying Reagent.

The surface modifying reagent is a compound having a structure LG-(L")$_j$-R$_x$ (Formula 4). The linking group LG links covalently to the oxides of the surface of the substrate. The substrate may be a DEP-configured substrate and may include silicon or alumina or hafnium oxide, and oxides may be present as part of the native chemical structure of the substrate or may be introduced as discussed herein. The linking group LG may be any linking group described herein, such as a siloxy or phosphonate ester group, formed from the reaction of a siloxane or phosphonic acid group with the oxide on the surface of the substrate. The reactive moiety $R_x$ is described above. The reactive moiety $R_x$ may be connected directly (L", j=0) or indirectly via a linker L" (j=1) to the linking group LG. The linking group LG may be attached to a first end of the linker L" and the reactive moiety $R_x$ may be connected to a second end of the linker L", which will be distal to the surface of the substrate once the surface modifying reagent has been attached to the surface as in Formula 6.

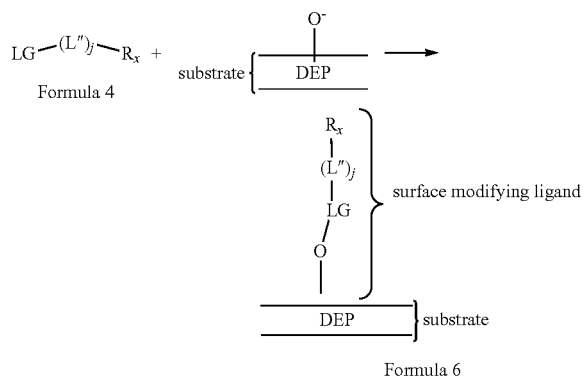

Formula 6

Linker L" may have a linear portion wherein a backbone of the linear portion includes 1 to 100 non-hydrogen atoms selected from of any combination of silicon, carbon, nitrogen, oxygen, sulfur and phosphorus atoms. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker L". In some embodiments, the backbone of the linker L" may include 10 to 20 atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

In some embodiments, the coating material (or surface modifying ligand) is deposited on the inner surfaces of the microfluidic device using chemical vapor deposition. Through chemical vapor deposition, the coating material can achieve densely-packed monolayers in which the molecules comprising the coating material are covalently bonded to the molecules of the inner surfaces of the microfluidic device. To achieve a desirable packing density, molecules comprising, for example, alkyl-terminated siloxane can be vapor deposited at a temperature of at least 110° C. (e.g., at least 120° C., 130° C., 140° C., 150° C., 160° C., etc.), for a period of at least 15 hours (e.g., at least 20, 25, 30, 35, 40, 45, or more hours). Such vapor deposition is typically performed under vacuum and in the presence of a water source, such as a hydrated sulfate salt (e.g., MgSO4.7H2O). Typically, increasing the temperature and duration of the vapor deposition produces improved characteristics of the hydrophobic coating material.

The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate). For example, such pre-cleaning can include a solvent bath, such as an acetone bath, an ethanol bath, or a combination thereof. The solvent bath can include sonication. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). The oxygen plasma cleaner can be operated, for example, under vacuum conditions, at 100 W for 60 seconds. Alternatively, liquid-phase treatments, which include oxidizing agents such as hydrogen peroxide to oxidize the surface, may be used in place of an oxygen plasma cleaner. For example, a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Deposition of a coating material comprising a densely-packed monolayer on a fully-assembled microfluidic circuit 120 may be beneficial in providing various functional properties. Without intending to be limited by theory, depositing such a coating material on a fully-assembled microfluidic circuit 120 may be beneficial in preventing delamination caused by a weakened bond between the microfluidic circuit material 116 and the electrode activation substrate 206/dielectric layer and/or the cover 110.

FIGS. 4A-4D depict cross-sectional views of microfluidic devices 500 comprising exemplary classes of coating materials. As illustrated, the coating materials 529 (shown schematically) can comprise a monolayer of densely-packed molecules covalently bound to both the inner surface 508 of the substrate 504 and the inner surface 509 of the cover 510 of the microfluidic device 500. The coating material 529 can be disposed on all inner surfaces 508, 509 proximal to, and facing inwards towards, the enclosure 502 of the microfluidic device 500, including, in some embodiments and as discussed above, the surfaces of microfluidic circuit material (not shown) used to define circuit elements and/or structures within the microfluidic device 500. In alternate embodiments, the coating material 529 can be disposed on only one or some of the inner surfaces of the microfluidic device 500.

Figure 4A:
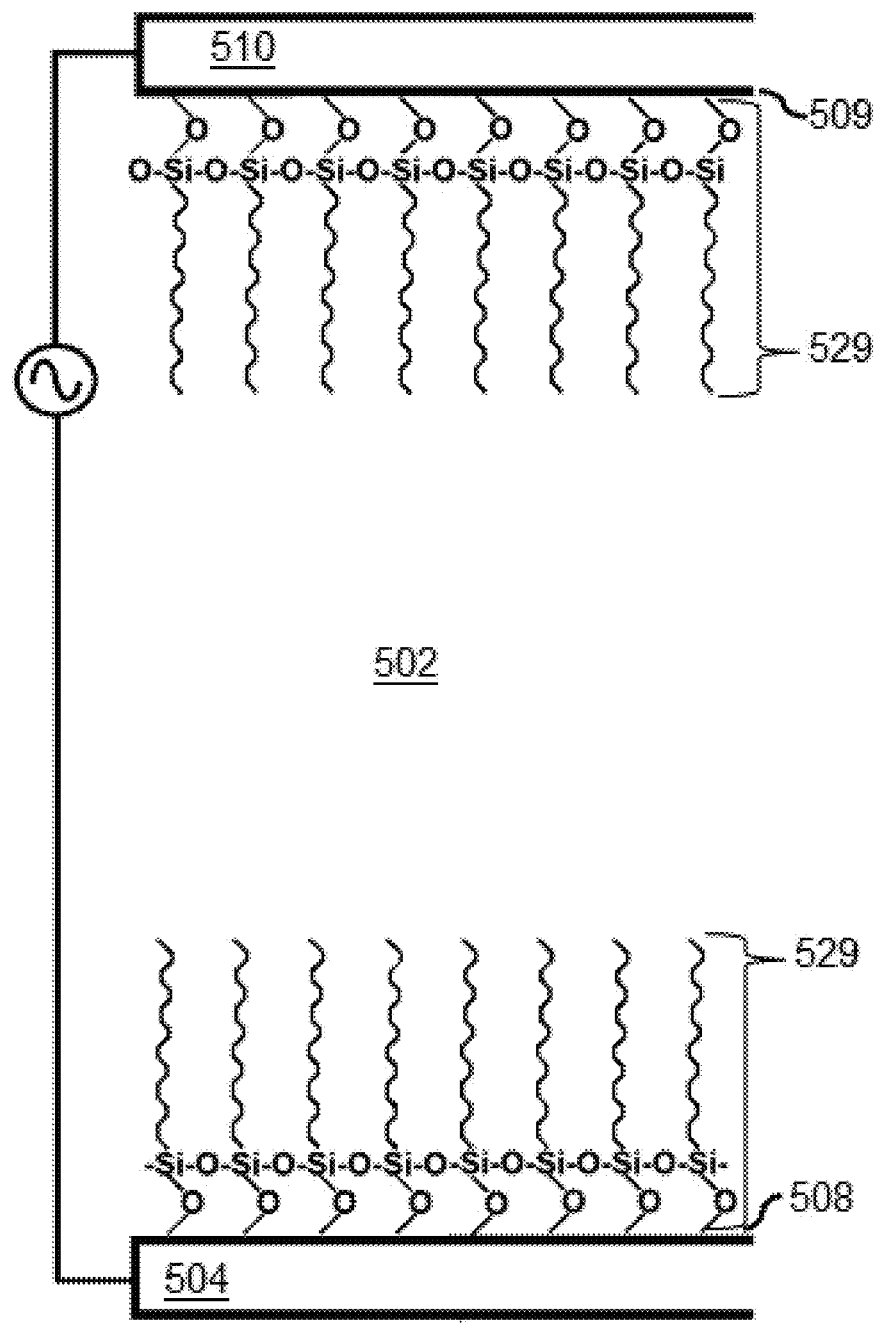
FIGS. 4A, 4B, 4C and 4D illustrate inner surfaces of a microfluidic device and blocking agents according to various specific embodiments of the invention.

In the embodiment shown in FIG. 4A, the coating material 529 comprises a monolayer of alkyl-terminated siloxane molecules, each molecule covalently bonded to the inner surfaces 508, 509 of the microfluidic device 500 via a siloxy group. However, any of the above-discussed coating materials 529 can be used (e.g. alkyl-terminated phosphonate ester molecules). More specifically, the alkyl group can comprise a linear chain of at least 10 carbon atoms (e.g. 10, 12, 14, 16, 18, 20, 22, or more carbon atoms) and, optionally, may be a substituted alkyl group. As discussed above, coating materials 529 that comprise a monolayer of densely-packed molecules can have beneficial functional characteristics for use in DEP configured microfluidic devices 500, such as minimal charge trapping, reduced physical/electrical thickness, and a substantially uniform surface.

In some embodiments, the coating material 529 used to coat the inner surface(s) 508, 509 of the microfluidic device 500 provides a functional benefit of reducing nuclei adhesion. In a specific embodiment, the coating material 529 can comprise a fluoroalkyl group (e.g. a fluorinated alkyl group or a perfluorinated alkyl group) at its enclosure-facing terminus (i.e. the portion of the monolayer of the coating material 529 that is not bound to the inner surfaces 508, 509 and is proximal to the enclosure 502). As discussed above, the coating material 529 can comprise a monolayer of fluoroalkyl-terminated siloxane or fluoroalkyl-terminated phosphonate ester, wherein the fluoroalkyl group is present at the enclosure-facing terminus of the coating material 529. Such a coating material 529 provides a functional benefit in reduced fouling and, more generally, reduced adhesion of biological molecules such as those present on the outer membranes of nuclei.

In some embodiments, the coating material 529 used to coat the inner surfaces 508, 509 of the microfluidic device 500 provides a functional benefit in presenting one or more moieties that can bind a blocking agent in a blocking solution. Depending on the embodiment, the coating material 529 may comprise or be chemically modified (e.g. by reaction) to present a moiety comprising a cation ("cationic moiety") (e.g. a quaternary ammonium group) at its enclosure-facing terminus. In some embodiments, the coating material 529 may comprise or be chemically modified to present a moiety comprising an anion ("anionic moiety"), such as a phosphonic acid, carboxylic acid, or sulfonic acid moiety, at its enclosure-facing terminus. In some embodiments the coating material 529 may comprise or be chemically modified to present a mixture of cations and anions at its enclosure-facing termini.

Figure 4B:
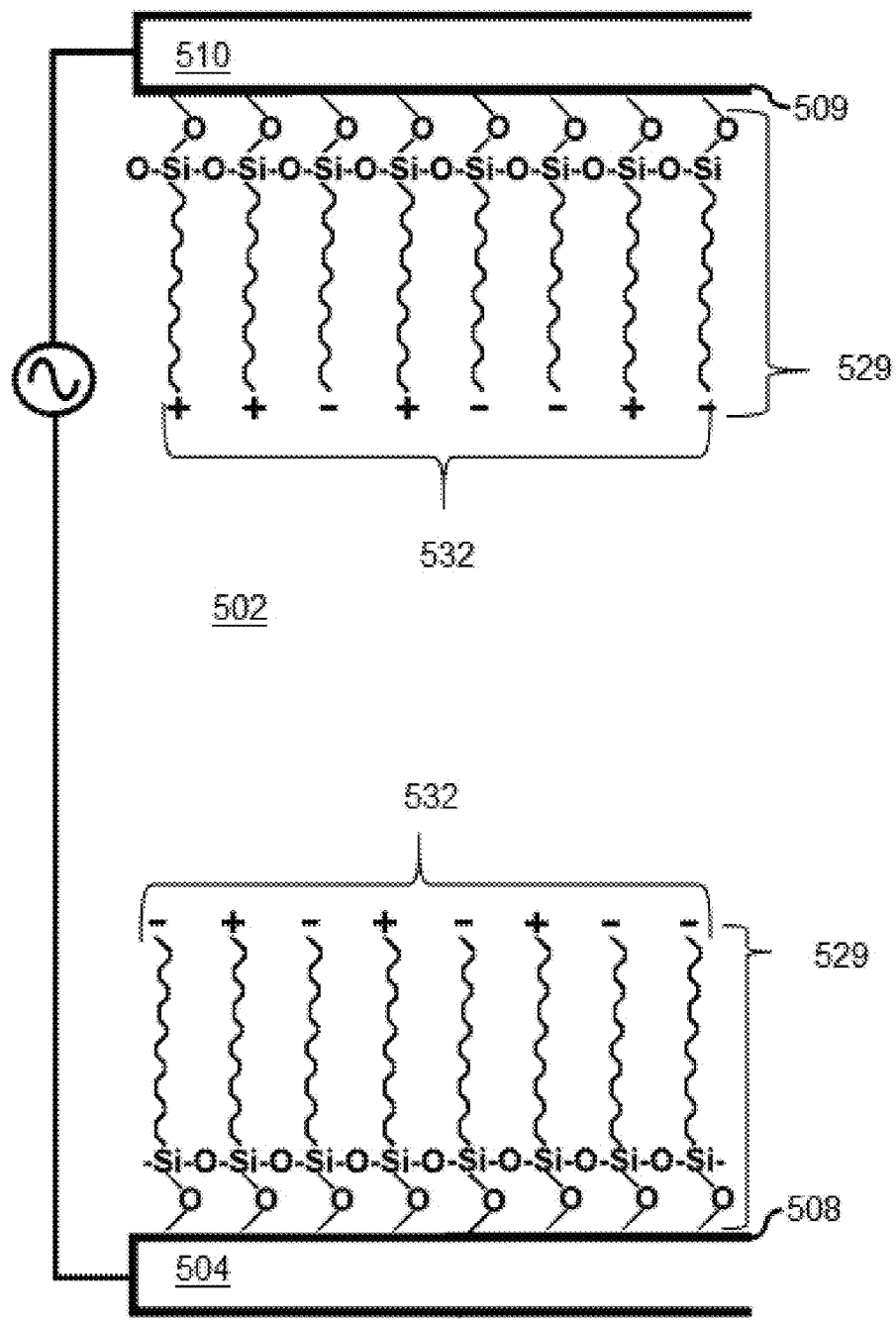

FIG. 4B provides a schematic illustration of a specific embodiment where the monolayer of coating material 529 comprises or has been chemically modified to present a mixture of moieties 532 comprising cations (represented with a "+") and anions (represented with a "−") at the enclosure-facing termini of its alkyl groups. Without intending to be limited by theory, by presenting both cationic and anionic moieties proximal to the enclosure 502 of the microfluidic circuit 500, the coating material 529 can form strong hydrogen bonds with water molecules such that the resulting water of hydration acts as a layer (or "shield") that separates the nuclei from interactions with non-biological molecules (e.g., the silicon and/or silicon oxide of the substrate). In addition, in embodiments in which the coating material 529 is used in conjunction with blocking agents, the anions and cations of the coating material 529 can form ionic bonds with the charged portions of blocking agents (e.g. proteins in solution) that are present in a medium 180 (e.g. a blocking solution) in the enclosure 502.

Figure 4C:
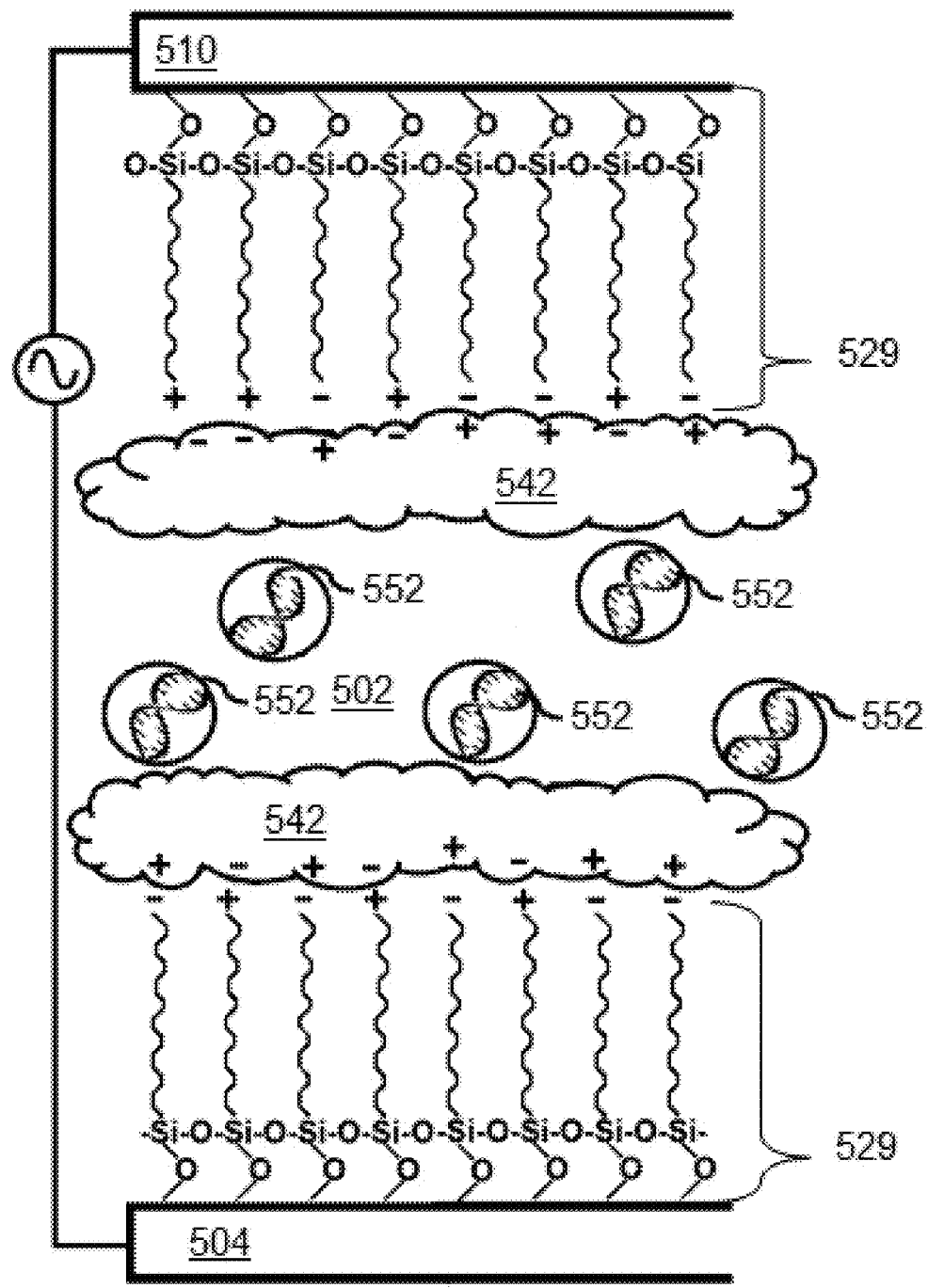

FIG. 4C illustrates an embodiment of FIG. 4B in which the monolayer of coating material 529 comprising anionic and cationic moieties is used to bind a blocking agent 542. As illustrated in FIG. 4C, the charged portions (i.e. the regions of the blocking agent 542 that present cations and/or anions) of the blocking agent 542 form ionic bonds with both the cationic moieties and the anionic moieties in the coating material 529. Providing that the nuclei 552 within the enclosure 502 do not bind to the blocking agent 542, the presence of the blocking agent 542 at the surface of the coating material 529 will prevent the nuclei 552 from adhering to the inner surfaces 508, 509 of the microfluidic device 500.

Figure 4D:
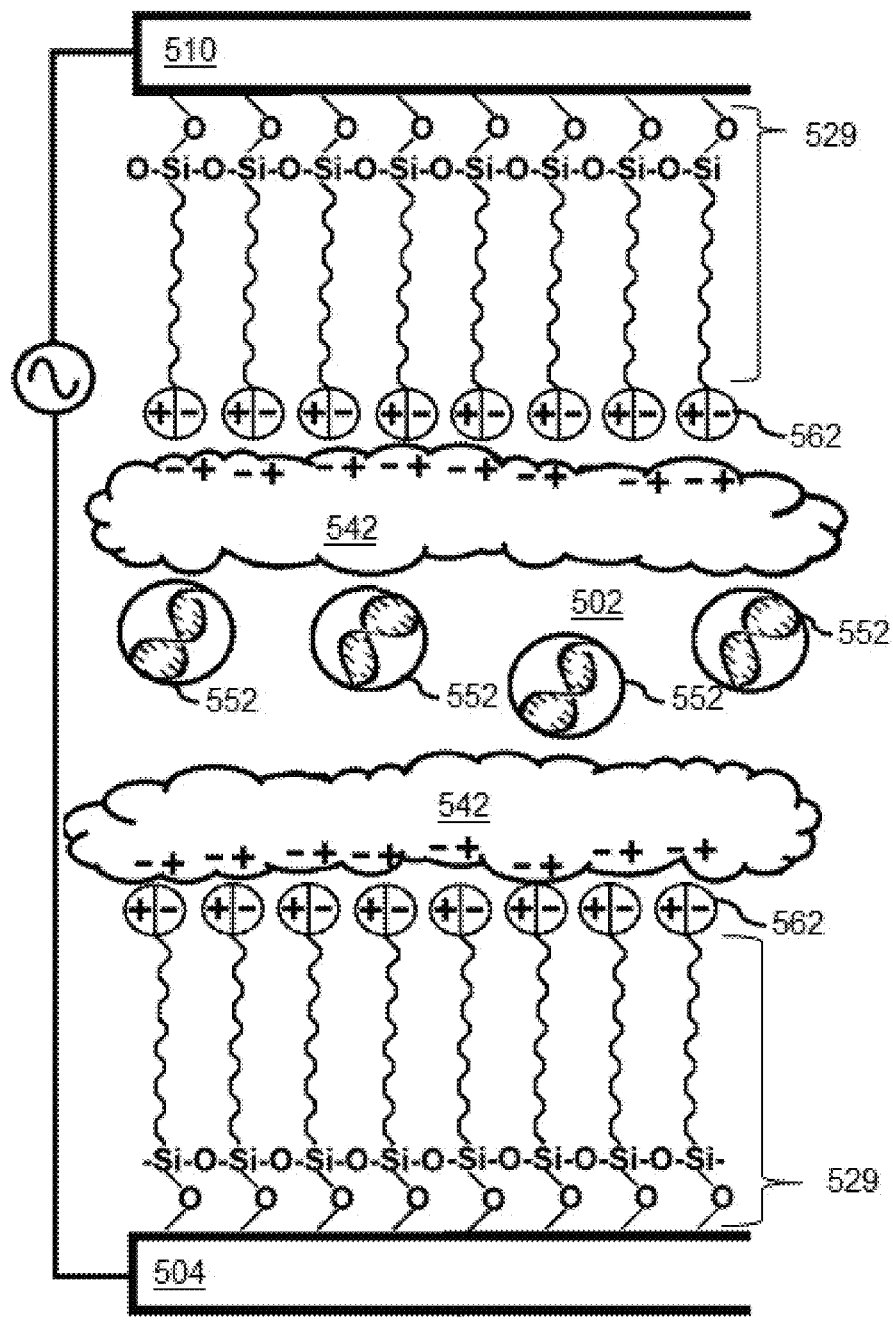

In some embodiments, the coating material 529 may comprise or be chemically modified to present a moiety comprising a zwitterion ("zwitterionic moiety") at its enclosure-facing terminus. Non-limiting examples of zwitterionic moieties include: carboxybetaines, sulfobetaines, sulfamic acids, and amino acids. FIG. 4D illustrates an embodiment in which the coating material 529 comprises zwitterionic moieties. Similar to the discussion relating to cation and anion moieties, the zwitterionic moieties can form strong hydrogen bonds with water molecules such that the resulting water of hydration acts as a layer (or "shield") that separates the nuclei from interactions with non-biological molecules (e.g., the silicon and/or silicon oxide of the substrate). In addition, as illustrated in FIG. 4D, the zwitterionic moieties can also form ionic bonds with the charged portions of a blocking agent 542. As discussed in regard to FIG. 4C, the binding of the blocking agent 542 to the zwitterionic moieties can help prevent the nuclei 552 from adhering to the inner surfaces 508, 509 of the microfluidic device 500.

In some embodiments, the coating material may comprise or be chemically modified to present a blocking agent at its enclosure-facing terminus. In some embodiments, the blocking agent may be an alkylene ether containing polymer, such as PEG. In some embodiments, the blocking agent may be a polysaccharide, such as dextran.

By ensuring that the nuclei do not adhere to the inner surfaces 508, 509 of the microfluidic device 500, nuclei 552 may be repositioned using DEP force (e.g. OET force) and/or fluid flow in the microfluidic device 500. Such repositioning can be prior to and/or after the selection of nuclei based on specific characteristics. For example, individual nuclei 552 may be repositioned to sequestration pens or other areas of the microfluidic device 500 using DEP force and then assayed (or otherwise analyzed) for a characteristic used to select the nuclei. Similarly, individual nuclei 552 may be exported from sequestration pens or other areas of the microfluidic device using DEP force so that they can be further analyzed.

Selection and Repositioning of Nuclei.

In some embodiments, one or more characteristics can be used to identify a cell nucleus 552 of interest that is to be selected, e.g., a cell nucleus having a pre-determined or pre-specified characteristic. The selected cell nucleus can then be repositioned for further analysis. The one or more characteristics can include any detectable characteristic of the cell nucleus, including morphological characteristics (e.g. size, shape, etc.), color of the cell nucleus, and/or fluorescent or visible light absorption/emission characteristics (e.g., associated with a marker, such as a fluorescently labeled marker).

In some embodiments, a cell nucleus/nuclei are contacted (i.e. "labelled") with a detectable binding agent that is specific for a cell nucleus target (or analyte) of interest (which can be on the surface of or inside the cell nucleus). For example, a cell nucleus/nuclei can be labelled with a detectable binding agent (e.g., a stain, fluorescently-labeled antibodies, or the like) to distinguish nuclei originating from different types of cells or to distinguish nuclei from other micro-objects in a sample. In some embodiments, labelling can be performed prior to introducing the nuclei into the microfluidic device. In some embodiments, labelling can be performed after introducing nuclei into the microfluidic device (e.g., after moving the nuclei into the flow region or into an isolation region in a sequestration pen). Detectable binding agents including any agent that binds to a target/analyte and that can be detected in the microfluidic device. Non limiting examples of binding agents include polypeptides (e.g., antibodies or antigen binding fragments thereof, ligands, receptors, virus particles), polynucleotides (e.g., DNA probes, RNA probes, hybrid DNA/RNA probes, probes containing non-naturally occurring backbone linkages, e.g., PNA, and the like), polysaccharides, small molecules, and the like. In many embodiments, such binding agents include a target specific binding region attached to detectable label, e.g., a fluorescent label, where the attaching can be covalent or non-covalent (e.g., using a binding pair, e.g., biotin/streptavidin). Further, the cell nuclei may include gene products that are detectable without the need for contacting them with a specific binding agent, e.g., fluorescent proteins or enzymes with detectable activity on a natural or synthetic substrate that produces a detectable product. No limitation in this regard is intended.

Depending on the embodiment, one or more nuclei can be selected based on a combination of morphological characteristics (e.g. size and shape) and characteristics associated with a detectable binding agent or a detectable gene product (e.g. a quantity or intensity of a detectable binding agent or a detectable gene product). For example, nuclei of anaplastic cancer cells are both larger and contain more nucleic acid than nuclei from non-cancerous cells and may be identified based on a combination of size and the intensity of a detectable binding agent that binds nucleic acid. In some embodiments, nuclei may be selected automatically based on a combination of pre-specified characteristics.

In some embodiments, the characteristic(s) used to select nuclei may be identified using machine learning algorithms. In these embodiments, an individual may annotate nuclei that belong to a specific class of nuclei and one or more machine learning algorithms may be used to computationally identify one or more characteristics that distinguish the class of nuclei from nuclei that don't belong to the same class. For example, a pathologist could annotate several nuclei that belong to the same class of nuclei and a machine learning algorithm could be applied to an image of the annotated nuclei (or a set of features generated from an image of the annotated nuclei) to determine specific characteristics that distinguish (or a combination of characteristics that distinguish) the class of annotated nuclei from other nuclei. Suitable machine learning algorithms for this purpose include support vector machines (SVMs), neural networks (e.g. convolutional neural networks (CNNs)), and Bayesian networks. Other machine learning algorithms are known in the art.

In certain embodiments, the microfluidic device comprises a plurality of sequestration pens in fluid connection with the flow channel, where each sequestration pen of the plurality has a corresponding isolation region. Such configurations allow for the isolation and selection of many distinct individual nuclei or distinct populations or "classes" of nuclei. Thus, in some embodiments the flow medium introduced into the microfluidic device includes a plurality of cell nuclei (from one or more cell sources) and includes moving each of the plurality of cell nuclei into a corresponding isolation region of a sequestration pen. In some embodiments, only one cell nucleus is moved to an isolation region of a sequestration pen, while in other embodiments, multiple cell nuclei are moved to an isolation region of a sequestration pen. It is to be understood that any number of nuclei may be moved into each different isolation regions of the plurality of sequestration pen. Thus, once the cell nuclei are isolated in the microfluidic device, any given sequestration pen may include no cell nucleus, one cell nucleus, or multiple cell nuclei. No limitation in this regard is intended. For example, in some embodiments, the plurality of cell nuclei may be isolated and selected in any type of chamber or other holding area of the microfluidic device.

Where a plurality of cell nuclei are being isolated, and where the microfluidic device includes a plurality of sequestration pens, the method can include selecting a first sub-set of cell nuclei from the plurality of cell nuclei that have a first predetermined characteristic, and moving the selected first sub-set of cell nuclei to the corresponding isolation region(s) of a first plurality of sequestration pens in the microfluidic device. In some embodiments, a second sub-set of cell nuclei from the plurality of cell nuclei that have a second predetermined characteristic can be selected and moved to the corresponding isolation region(s) of a second plurality of sequestration pens in the microfluidic device. It is noted here that a predetermined characteristic can be a positive characteristic, e.g., binding of a particular binding agent, or a negative characteristic, e.g., not binding to a particular binding agent.

Once a cell nucleus is isolated, it can be employed in any downstream analysis or process of interest and/or stored (e.g., frozen) for future use. The analysis may be done while the nuclei are within the microfluidic device or after removal/export of the cell nuclei.

In some embodiments, a microfluidic device (or microchip) containing the isolated cell nuclei in the isolation region of the sequestration pens can be stored in any convenient manner such that the cell nuclei, or the components thereof, are maintained in a state that is amenable to a desired downstream process or analysis. For example, the microchip can be frozen to provide for storage of isolated cell nuclei. This process may include replacing the fluid in the microfluidic device with a storage buffer or removing the fluid.

In certain embodiments, one or more of the isolated cell nuclei are exported from the micro-fluidic device prior to performing a subsequent analysis or process. This process may include the use of any number of different forces, e.g., gravitational force, magnetic force, centrifugal force, DEP force (as detailed above), to move the cell nuclei out of the isolation region and into a flow region where the cell nuclei can be exported from the device through an outlet port. In some embodiments, DEP force is used to move single cell nuclei out of the sequestration pens or other areas of the microfluidic device in which they are located, thereby allowing for cell nuclei to be exported individually. In other embodiments, the export process might include disassembling the microfluidic device to retrieve the cell nuclei or opening a previously closed outlet port in communication with the isolation region of a sequestration pen which converts the isolation region from an unswept region to a swept region. Flowing a fluidic medium through the isolation region of the sequestration pen will move the cell nuclei through the outlet port thereby exporting the cell nuclei from the device. It is noted that in some situations, the cell nuclei may not need to be exported intact for downstream analysis or processing, and thus the nuclei can be disrupted and the subsequent cell nuclei contents retrieved (e.g., as a sample of proteins, nucleic acids, etc.). No limitation in this regard is intended.

Any desired cell nucleus or population of cell nuclei may be employed in the disclosed methods. As such, the cell nuclei can be derived from any nucleated cell (or eukaryotic cell) including nuclei derived from fungi, plants, protists, animals, etc. In many embodiments, cell nuclei are derived from a mammal, e.g., a human. Moreover, the cell nuclei can be from any type of sample having nucleated cells from a desired source. Thus, the cell nuclei can be obtained from fresh/live/viable cells (e.g., cells isolated from a fresh tissue sample or cells that have been grown in a medium ex vivo) or from cells that may be non-viable or compromised in some way (e.g., cells recently thawed from a previously frozen biopsy sample or chemically fixed cells). The nuclei can be separated from the plasma membranes, cytoplasm, and extracellular proteins and components using any convenient techniques known in the art.

In certain embodiments, the cell nuclei are derived from cells that are part of a particular tissue of a multicellular organism. When the cells are derived from an animal, such tissues include, but are not limited to: epithelial cell types (e.g., neuronal cell types, epidermal cells, cochlear hair cells, or the like), mesodermal cell types (e.g., muscle, fat, bone marrow, blood, or the like), endodermal cell types (e.g., intestinal cells or the like), blood cells (e.g., B cells, T cells, NK cells, macrophages), or tissues exhibiting a disease phenotype (e.g., cancer cells, inflamed cells, cells infected with a bacterial, fungal, protozoan, or viral pathogen).

For certain cell types, isolation of the cell nucleus may be preferable due to the impracticalities of isolating cells in their intact form. For example, certain cell types of interest may be in a tissue that is not amenable to dissociation and/or have a morphology that prevents efficient isolation procedures. One example is neuronal cells, which have morphological characteristics (e.g., dendrites and axons) that pose significant difficulty for efficient isolation.

In some embodiments, the cell nuclei are derived from a cancer cell or a cell suspected of being a cancer cell, e.g., from the affected tissue of a subject diagnosed with a cancer. Non-limiting examples of cancers in affected tissues include: breast cancer, large intestinal cancer, lung cancer, small lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, vaginal carcinoma, Hodgkin's disease, non-Hodgkin's lymphoma, esophageal cancer, small intestine cancer, endocrine cancer, thyroid cancer, parathyroid cancer, adrenal cancer, chronic or acute leukemia, soft tissue tumor, urethral cancer, penile cancer, prostate cancer, lymphocytic lymphoma, bladder carcinoma, kidney cancer, ureter cancer, renal carcinoma, renal pelvic carcinoma, CNS tumor, primary CNS lymphoma, bone marrow tumor, brain stem nerve gliomas, pituitary adenoma, testicular cancer, oral cancer, pharyngeal cancer, and uveal melanoma.

In some embodiments, the cell from which a cell nucleus is derived has been enriched, isolated, sorted, or otherwise manipulated prior to harvesting the cell nuclei. Any convenient method may be employed to achieve this, including but not limited to: antibody or binding agent-based methods (e.g., fluorescence activated cell sorting (FACS), magnetic activated cell sorting (MACS), panning, and the like), apheresis, centrifugation, elutriation, density gradient centrifugation, differential cell lysis protocols, differential growth medium and/or growth scaffolds, physical isolation (e.g., a clinical biopsy sample), etc. No limitation in this regard is intended.

Certain embodiments of the disclosed methods include harvesting one or more cell nuclei from one or more cells in a sample prior to introducing them into the microfluidic device for isolation. Any convenient cell nuclei isolation process may be employed, and generally will be dictated by the cell type from which the cell nucleus is being harvested as well as the state of the cells, e.g., whether the cells are in a viable or non-viable state. In general, harvesting cell nuclei can include any one or more of the following process steps: disrupting the cytoplasmic membrane and/or cell wall of a cell to release the cell nucleus/nuclei; contacting the cell nuclei with an enzyme (e.g., DNAse, collagenase, hyaluronidase); contacting the cell nuclei with a chelating agent (e.g., EDTA); washing the released cell nucleus/nuclei to remove cellular debris and cytoplasmic components; and placing the harvested cell nucleus/nuclei in a medium compatible with maintaining the cell nucleus/nuclei in a state that is conducive for isolation in a microfluidic device (e.g., a medium with one or more buffers and/or blocking agents, e.g., BSA, serum, polymers, detergents).

In certain embodiment, the cells from which the nuclei are derived are non-viable cells. In one example, cells derived from a formalin fixed paraffin embedded (FFPE) sample are processed to obtain a cell nuclei-containing sample that can be introduced into the microfluidic device. FFPE samples can be processed to obtain nuclei using any convenient protocol, including those described in PCT publication WO 2013123463 A1 (which includes de-waxing and rehydrating steps, hereby incorporate by reference herein).

The isolated cell nuclei can be used in any desired analysis or process. It is noted that while one or more assays/processes can be performed after isolation of the cell nucleus, in certain embodiments, the analysis is performed before/during the isolation step, e.g., when the detection of a particular predetermined characteristic of a cell nucleus is used to select and move the cell to an isolation region of a sequestration pen.

In certain embodiments, the isolated cell nuclei can be used to determine a genetic characteristic or analyze gene expression (either quantitatively or qualitatively). Any convenient genetic assay may be used, including those in which the cell nuclei are kept substantially intact, e.g., fluorescent in-situ hybridization (FISH), or those in which the cell nuclei are disrupted. It is noted that the analyses may be performed on an individual isolated cell nucleus or on one or more desired populations of isolated cell nuclei. Such analyses may also be done to compare one or more genetic characteristics between a first isolated cell nucleus/population of nuclei and a second isolated cell nucleus/population of nuclei. In some embodiments, the analyses is done to compare one or more genetic characteristic of one or more isolated cell nucleus/population of nuclei and a reference or control, e.g., the sequence of a gene known to be associated with a particular phenotype, e.g., a disease phenotype.

In certain embodiments, genetic analysis includes extracting nucleic acids from the isolated cell nucleus/nuclei, either DNA, RNA or both, and performing one or more genetic analysis tests on the extracted nucleic acids. Extracting the nucleic acids from the isolated cell nuclei can be achieved in any convenient manner. For example, the nuclei can be lysed/disrupted and the nucleic acids recovered using nucleic acid-binding beads or other reagents. In some embodiments, specific target nucleic acids are recovered, e.g., RNA, DNA, or specific sequences of interest, e.g., from a gene of interest or a genomic region of interest. The nuclei acids extracted from the isolated nuclei can be fragmented, e.g., by physical means or using nucleases, e.g., restriction enzymes. The extracted nuclei acids may be replicated, amplified, or reverse transcribed as desired and can be attached to adapters having functional sequences that can be used in downstream analysis, e.g., primer binding sites, barcodes, restriction enzyme sites, recombination sites, etc. In some embodiments, nucleic acids may be extracted and analyzed in a portion of the microfluidic device that is configured for electrowetting or opto-electrowetting (OEW).

Examples of the types of results that can be obtained include: copy number of a genetic region, a mutation (e.g., a somatic cell or inherited mutation), a duplication, a single nucleotide polymorphism, an insertion, an inversion, a nucleic acid modification, a chromosomal feature, a difference compared to a reference nucleic acid sample, epigenetic variation, gene expression (e.g., mRNA levels), and combinations thereof. In certain embodiments the genetic assay includes one or more of: nucleic acid sequencing analysis (e.g., whole genome or specific markers, such as disease markers), nucleic acid hybridization analysis, amplification reactions (e.g., PCR, RTPCR, linear amplification, etc.), and the like.

In certain embodiment, the cell nuclei, either before or after isolation, can be analyzed for a predetermined characteristic such as a marker or physical property of interest. Such markers/properties can be used to determine the type of cell from which the nucleus was derived and/or a phenotypic state of the cell, e.g., a disease phenotype. For example, cancer cells often have nuclei that are different in size and/or shape than normal cells. Thus, visual markers can be used to select nuclei of interest. In addition, the internal structure of cancer nuclei often differs from that of normal cells. Thus, staining for nuclear proteins (e.g., lamins A or B), nuclear membrane proteins (e.g., nuclear lamina-associated proteins, such as emerin), fibrillarin, nuclear pore proteins (NUPs, such as Nup153, Nup210, etc.), histone proteins, nuclear matrix proteins (e.g., p84) can highlight differences in nuclear structure. See, e.g., *Cancer Biology and the Nuclear envelope: Recent advances may elucidate past paradoxes*; Springer 2014; Eric C. Schirmer and Jose de las Heras (eds.) (hereby incorporated herein by reference) for a description of how the nuclear envelope and nuclear morphology can be used in the diagnosis of disease in a subject, including cancer. There are some cell-type specific markers that are found on or in nuclei that can be used to identify nuclei originating from a cell type of interest. Transcription factors are a common cell-type specific marker, but they can also include related proteins that bind and/or splice RNA (such as NeuN, the marker used in the example below). Additional structural characteristics can also be analyzed, including chromatin structure (e.g., related to histone binding), chromosomal configuration, size, shape, etc.

In certain embodiments, the isolated nuclei are used for functional studies, such as nuclear transfer for cloning, as suggested in US 20040148648; Kim J and Zaret K S, *Reprogramming of human cancer cells to pluripotency for models of cancer progression.* EMBO J. 2015 Mar. 12; 34(6):739-747; and Tamada H, Kikyo N, *Nuclear reprogramming in mammalian somatic cell nuclear cloning.* Cytogenet Genome Res. 2004; 105 (2-4):285-91.

Figure 5:
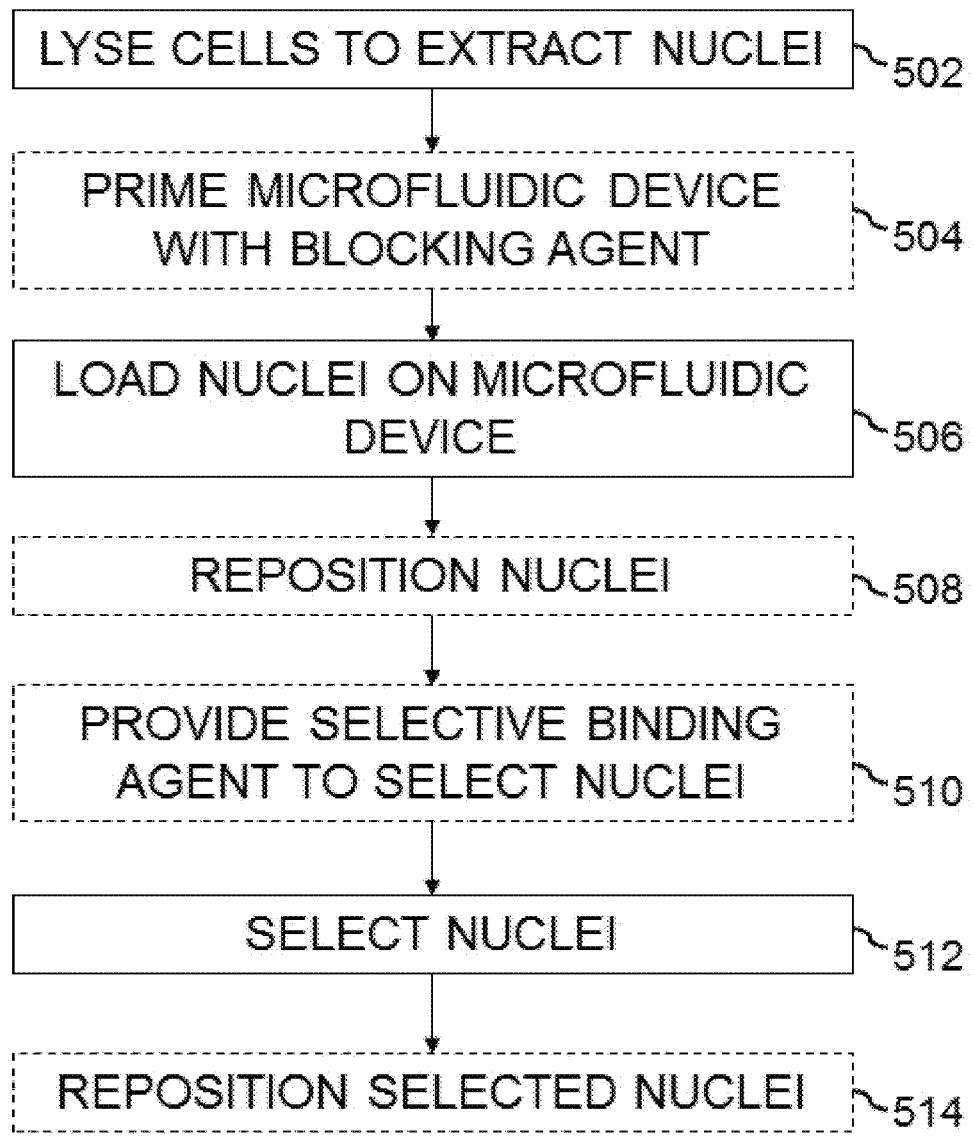
FIG. 5 illustrates steps performed to select nuclei according to a specific embodiment of the invention.

FIG. 5 illustrates various steps performed to select nuclei in a microfluidic device according to some embodiments of the present invention. As discussed below and as can be appreciated by those skilled in the art, only some of the steps may be performed and the steps may be performed in a different order than shown. In addition, some or all of the steps discussed below may be automated.

At step 502, a plurality of cells are lysed to extract a plurality of nuclei. As discussed above, any type of cell comprising a nucleus can be lysed. In some instances, the plurality of cells are a homogeneous population of cells (i.e. the cells are all the same type of cell). In some instances, the cells are a heterogeneous population of cells. For example, a blood sample from a subject with cancer may comprise circulating tumor cells, white blood cells and red blood cells. Similarly, a fine needle aspirate ("FNA") tumor sample derived from a patient may contain blood cells and tissue cells as well as tumor cells.

Depending on the embodiment and the functionality required, a number of different lysing agents may be used to lyse the cells and extract the nuclei. In some embodiments, a non-ionic detergent is used to perform cell lysis. In a specific embodiment, a one to ten percent solution of Trition X-100 is used to perform cell lysis. In another embodiment, a one to ten percent solution of NP40 is used to perform cell lysis. In some embodiments, a hypotonic buffer is used to perform cell lysis. In a specific embodiment, double distilled water ("ddH2O") is used to lyse the cells. In some embodiments, a hypotonic buffer is combined with a weak detergent to lyse the cells.

In most embodiments, the nuclei will be lysed outside of the microfluidic device ("off-chip"), prior to importing the nuclei into the microfluidic device. As discussed above, off-chip lysis is beneficial because many cell types are difficult to manipulate within the microfluidic device. However, in other embodiments, it may be beneficial to load cells on the microfluidic device and perform lysis within the microfluidic device.

At step 504, the microfluidic device is optionally primed with the blocking agent and/or blocking solution prior to loading cells/nuclei onto the chip. In some embodiments, the microfluidic device may be primed with a blocking agent and/or blocking solution that is provided to the microfluidic device for a duration of time (i.e. perfused throughout a microfluidic circuit of the microfluidic device for a duration of time). As discussed above, in some embodiments, a blocking agent can bind to the inner surface(s) of the microfluidic device and thus block nuclei adhesion to one or more of the inner surfaces of the microfluidic device. In alternate embodiments, the microfluidic device is not primed with the blocking agent and/or blocking solution, but instead, the blocking agent and/or blocking solution is provided to the microfluidic device at the same time as the nuclei are loaded into the microfluidic device. In other embodiments, the inner surface(s) of the microfluidic device can comprise a covalently bound coating material, which can be any of the coating materials described herein. In still other embodiments, the inner surface(s) of the microfluidic device can comprise a covalently bound coating material that is bound to blocking agent and/or blocking solution (e.g., via hydrogen bonds and/or ionic bonds).

At step 506, the nuclei are loaded into the microfluidic device. As discussed above the nuclei may be introduced to the microfluidic device by providing the nuclei in a flow of medium, by using other forces (e.g. gravity) to load the nuclei, or by using a combination of a flow of medium and other forces.

At step 508, the nuclei are repositioned within the microfluidic device. Depending on the embodiment, the nuclei can be repositioned using any kind of force (e.g. gravity). In some embodiments, the nuclei can be repositioned using OET force. In some embodiments, the nuclei may be automatically repositioned into specific areas of the microfluidic device (e.g. sequestration pens or holding areas). In some embodiments, the nuclei may be automatically identified prior to repositioning the nuclei. Methods of automatically identifying and repositioning micro-objects such as nuclei are discussed in U.S. patent application Ser. No. 14/963,230, the entirety of which is herein incorporated by reference.

At step 510, the nuclei are optionally provided (i.e. labelled with) a selective binding agent that is used to determine one or more characteristics of some or all of the nuclei (e.g. amount of DNA in the nuclei, the cell type of the nuclei, etc.). As discussed above, the nuclei can be contacted with the selective binding agent at any time (e.g., prior to loading the nuclei on the chip, prior to repositioning the nuclei on the chip, or after repositioning the nuclei on chip but before further repositioning of the nuclei).

At step 512, the nuclei are selected based on one or more characteristics of the nuclei. As discussed above, the nuclei may be selected based on characteristics such as the morphology of the nuclei or characteristics based on the selective binding agent (e.g. the intensity of the selective binding agent). Similarly, the characteristics used to select the nuclei may be identified through machine learning techniques.

At step 514, the selected nuclei are optionally repositioned for further analysis (e.g. additional assays, DNA sequence analysis). In some embodiments, the selected nuclei may be repositioned from a flow region, such as a channel, into a sequestration pen. In other embodiments, the selected nuclei may be repositioned into a channel for export and analysis. In other embodiments, the selected nuclei may be transferred from a first sequestration pen to a second sequestration pen. In still other embodiments, the selected nuclei may be repositioned from a flow region (e.g., channel) or sequestration pen, either or both of which may have a dielectrophoresis (DEP) configuration, to an area or portion of the same microfluidic device having an electrowetting (EW) or opto-electrowetting (OEW) configuration or a different device having an electrowetting (EW) or opto-electrowetting (OEW) configuration. The repositioning can involve using dielectrophoretic force to move the nuclei. In a specific embodiment, nuclei that have been repositioned to a flow region, such as a channel, may be further repositioned (e.g., exported) by providing a flow of medium in the channel.

EXAMPLES

The following examples are put forth so as to provide those of ordinary skill in the art with disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1—Selection, Isolation, and Export of Neuronal Nuclei

A microfluidic device (Berkeley Lights™), having a single flow region with four parallel flow channels and approximately 1000 sequestrations pens, was flushed with 100% $CO_2$, then primed with priming medium (i.e., Dubelco's PBS with Magnesium Chloride and Calcium Chloride (DPBS)+5 mg/ml BSA+0.1% Pluronic F127).

Human brain tissue was snap frozen and dissected on dry ice. Small pieces of this human brain tissue was thawed, as needed, and homogenized to obtain cell nuclei.

The nuclei were incubated with NeuN-specific antibody labeled with Alexa 485 to allow detection in the device using fluorescence emission (FITC channel). Following the incubation, stained nuclei were pelleted by centrifugation, the resulting supernatant was removed, and the stained nuclei were resuspended in blocking buffer containing Dubelco's PBS with Magnesium Chloride and Calcium Chloride (DPBS)+5 mg/ml BSA+30% Goat Serum+1.0% Pluronic® F127+200 U/ml DNAse. Stained nuclei were incubated in blocking buffer for 15 minutes, then flowed into the microfluidic device in the same buffer.

Once in the flow channels of the microfluidic device, stained neural nuclei were detected using the FITC channel. The observed neural nuclei were 5-10 μm in diameter. Individual neural nuclei were selected and moved into the isolation regions of sequestration pens using OET (see FIG. 5). OET was performed with a 10× microscope objective, at a voltage of 8V ppk (peak-to-peak) and a frequency of 1000 kHz.

Figure 6:
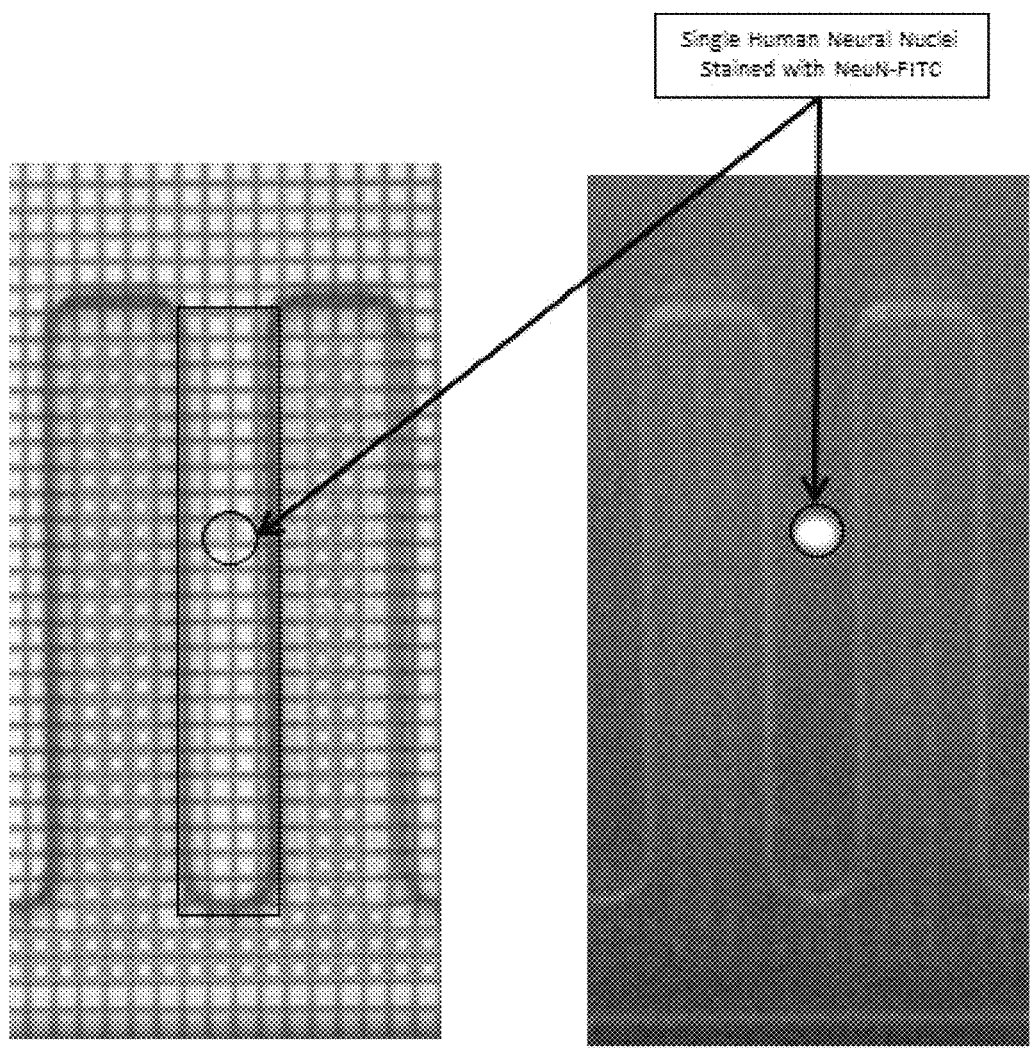
FIG. 6 shows an image of a sequestration pen of a microfluidic device according to the present disclosure, with a cell nucleus stained with anti-NeuN-FITC antibody under visible light (left) and fluorescent light to detect FITC (right).
Figure 7:
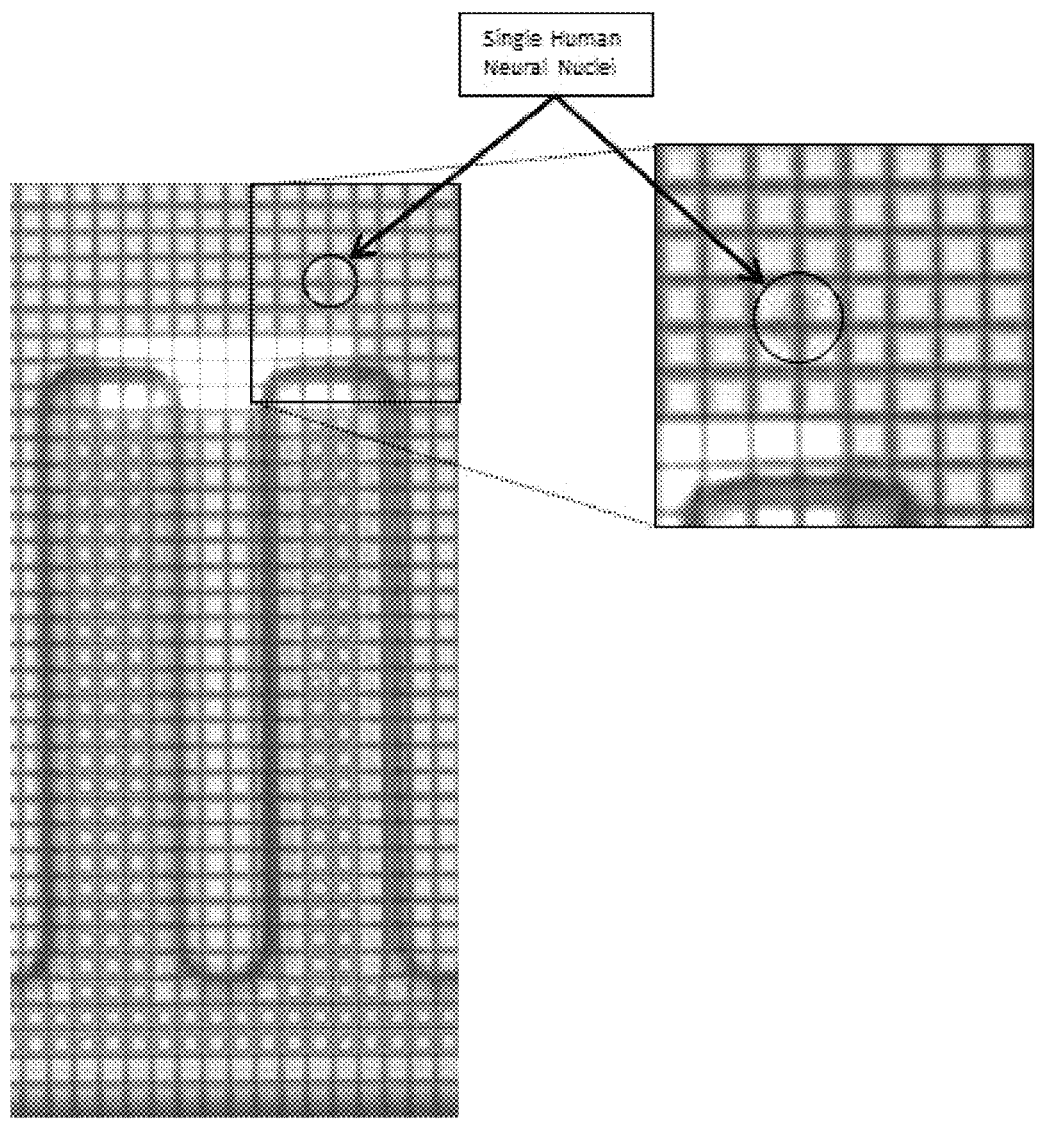
FIG. 7 shows the cell nucleus of FIG. 6 after movement using OET.

After a sufficient number of neural nuclei were sequestered in the sequestration pens, the flow channels were flushed with priming medium supplemented with 30% goat serum to remove unwanted cell nuclei and other debris. After flushing the flow channels, select nuclei were moved out of their sequestration pens and into their corresponding flow channel using OET (FIG. 6), whereupon they were individually exported (by fluidic flow) from the microfluidic device into wells of a micro-titer plate. The OET was performed with the same settings used for loading nuclei into the sequestration pens and a 30 micron OET bar (see FIG. 6).

It was observed that 50%-60% of nuclei could be successfully moved and exported. In contrast, in the absence of 30% goat serum, cell nuclei imported into the microfluidic device settled on the surface of the flow channel and became immovable stuck.

Exported nuclei were subject to DNA sequencing.

Example 2—Selection, Isolation, and Export of Neuronal Nuclei

A microfluidic device (Berkeley Lights™), having a single flow region with four parallel flow channels and approximately 1000 sequestration pens, is flushed with 100% $CO_2$, then primed with priming medium (i.e., Dubelco's PBS with Magnesium Chloride and Calcium Chloride (DPBS)+70 mg/ml BSA+1.0% Pluronic F127).

Human brain tissue is snap frozen and dissected on dry ice. Small pieces of this human brain tissue is thawed, as needed, and homogenized to obtain cell nuclei.

The nuclei are incubated with NeuN-specific antibody labeled with Alexa 485 to allow detection in the device using fluorescence emission (FITC channel). Following the incubation, stained nuclei are pelleted by centrifugation, the resulting supernatant is removed, and the stained nuclei are resuspended in blocking buffer containing Dubelco's PBS with Magnesium Chloride and Calcium Chloride (DPBS)+ 70 mg/ml BSA+1.0% Pluronic® F127+200 U/ml DNAse. Stained nuclei are incubated in blocking buffer for 15 minutes, then flowed into the microfluidic device in the same buffer.

Once in the flow channels of the microfluidic device, stained neural nuclei are detected using the FITC channel. Individual neural nuclei are selected and moved into the isolation regions of sequestration pens using OET. OET is performed with a 10× microscope objective, at a voltage of 8V ppk (peak-to-peak) and a frequency of 1000 kHz.

After a sufficient number of neural nuclei are sequestered in the sequestration pens, the flow channels are flushed with priming medium supplemented with 30% goat serum to remove unwanted cell nuclei and other debris. After flushing the flow channels, select nuclei are moved out of their sequestration pens and into their corresponding flow channel using OET, whereupon they are individually exported (by fluidic flow) from the microfluidic device into wells of a micro-titer plate. The OET is performed with the same settings used for loading nuclei into the sequestration pens and a 30 micron OET bar.

Exported nuclei can be subject to DNA sequencing or other downstream analyses/processes as desired.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of isolating a cell nucleus, said method comprising:
    providing a microfluidic device comprising:
        a flow region containing a first liquid medium;
        a first sequestration pen comprising an isolation region and a connection region, wherein the connection region has a proximal opening to the flow region and a distal opening to the isolation region and the isolation region opens to the connection region; and
        a substrate comprising a covalently linked coating material,
        wherein said isolation region of said first sequestration pen is an unswept region of said first sequestration pen, and wherein said substrate is configured to selectively generate forces capable of moving cell nuclei;
    flowing the first liquid medium comprising a cell nucleus into said flow region, said cell nucleus separated from a cell; and
    moving said cell nucleus from said flow region to said isolation region of said first sequestration pen using forces generated by the substrate, thereby isolating said cell nucleus.

2. The method of claim 1, wherein moving said cell nucleus from said flow region to said isolation region of said first sequestration pen comprises using dielectrophoresis (DEP) forces selectively generated by said substrate, wherein said DEP forces attract or repel said cell nucleus.

3. The method of claim 1, wherein said flow region comprises a flow channel in fluid connection with said isolation region of said first sequestration pen, and wherein flowing the first liquid medium comprising said cell nucleus comprises flowing said first liquid medium into said flow channel.

4. The method of claim 1, further comprising detecting a characteristic of said cell nucleus.

5. The method of claim 4, wherein said detecting is performed prior to said moving.

6. The method of claim 3, wherein said micro-fluidic device comprises a plurality of sequestration pens in fluid connection with said flow channel, each sequestration pen of said plurality having a corresponding isolation region.

7. The method of claim 6, wherein said first liquid medium comprises a plurality of cell nuclei and said method further comprises:
    moving said plurality of cell nuclei into said corresponding isolation region(s) of one or more sequestration pens of said plurality.

8. The method of claim 7, further comprising selecting a first sub-set of cell nuclei from said plurality of cell nuclei that have a first predetermined characteristic, and moving said selected first sub-set of cell nuclei to the corresponding isolation region(s) of one or more first sequestration pens of said plurality of sequestration pens.

9. The method of claim 7, wherein only one cell nucleus is moved to said corresponding isolation region of each sequestration pen of said plurality.

10. The method of claim 4, wherein said detecting comprises contacting said cell nucleus with a detectable binding agent.

11. The method of claim 1, further comprising determining a genetic characteristic of said isolated cell nucleus.

12. The method of claim 11, wherein said isolated cell nucleus is exported from said micro-fluidic device prior to performing said determining.

13. The method of claim 1, wherein said cell nucleus is derived from a mammal or a human.

14. The method of claim 1, further comprising: harvesting said cell nucleus from said cell.

15. The method of claim 1, wherein the cell nucleus is derived from a live cell.

16. The method of claim 1, wherein the cell nucleus is derived from a non-viable cell.

17. The method of claim 16, wherein said non-viable cell is a cell that has been frozen and thawed.

18. The method of claim 16, wherein said non-viable cell is a cell that has been chemically fixed.

19. The method of claim 1, wherein the cell nucleus is derived from a cancer cell.

20. The method of claim 1, wherein the coating material comprises a polymer comprising alkylene ether moieties, saccharide moieties, or amino acid moieties.

21. The method of claim 20, wherein the coating material comprises dextran.

22. The method of claim 20, wherein the coating material comprises poly-ethylene glycol.

23. The method of claim 1, wherein the isolation region comprises a single opening to the connection region.

24. The method of claim 1, wherein the microfluidic device comprises a cover, a microfluidic structure containing the flow region and the first sequestration pen, and a bottom support structure.

25. The method of claim 1, wherein a width $W_{con}$ of the connection region of the sequestration pen at the proximal opening to the flow region is from about 20 to about 100 microns.

26. The method of claim 1, wherein a ratio of a length $L_{con}$ of the connection region of the sequestration pen to a width $W_{con}$ of the connection region at the proximal opening to the flow region is at least about 1.0, about 1.5, or about 2.0.

* * * * *